(12) United States Patent
Markham et al.

(10) Patent No.: US 11,419,928 B2
(45) Date of Patent: Aug. 23, 2022

(54) METHODS AND COMPOSITIONS FOR TREATING CANCER

(71) Applicant: The Johns Hopkins University, Baltimore, MD (US)

(72) Inventors: Richard Markham, Columbia, MD (US); James Gordy, Baltimore, MD (US)

(73) Assignee: The Johns Hopkins University

( * ) Notice: Subject to any disclaimer, the term of this patent is extended or adjusted under 35 U.S.C. 154(b) by 283 days.

(21) Appl. No.: 16/170,534

(22) Filed: Oct. 25, 2018

(65) Prior Publication Data

US 2019/0167775 A1 Jun. 6, 2019

Related U.S. Application Data

(60) Provisional application No. 62/576,986, filed on Oct. 25, 2017.

(51) Int. Cl.
| | |
|---|---|
| *A61K 31/712* | (2006.01) |
| *A61K 39/00* | (2006.01) |
| *A61K 39/39* | (2006.01) |
| *A61K 39/385* | (2006.01) |
| *C07K 14/47* | (2006.01) |
| *A61P 35/00* | (2006.01) |
| *A61K 47/64* | (2017.01) |

(52) U.S. Cl.
CPC ...... *A61K 39/00119* (2018.08); *A61K 39/001192* (2018.08); *A61K 39/385* (2013.01); *A61K 39/39* (2013.01); *A61K 47/6425* (2017.08); *A61P 35/00* (2018.01); *C07K 14/4748* (2013.01); *A61K 31/712* (2013.01); *A61K 2039/53* (2013.01); *A61K 2039/545* (2013.01); *A61K 2039/55516* (2013.01); *A61K 2039/55522* (2013.01); *A61K 2039/55561* (2013.01); *A61K 2039/572* (2013.01); *A61K 2039/6031* (2013.01)

(58) Field of Classification Search
CPC .............................................. A61K 39/00119
USPC ..................................................... 424/184.1
See application file for complete search history.

(56) References Cited

U.S. PATENT DOCUMENTS

| | | | |
|---|---|---|---|
| 6,406,705 | B1 | 6/2002 | Davis et al. |
| 8,742,088 | B2 | 6/2014 | Durrant et al. |
| 9,404,925 | B2 | 8/2016 | Nakatsura et al. |
| 2002/0193330 | A1 | 12/2002 | Hone et al. |
| 2005/0266012 | A1 | 12/2005 | Andrieu et al. |
| 2007/0298051 | A1 | 12/2007 | Barouch et al. |
| 2008/0044418 | A1 | 2/2008 | Dranoff et al. |
| 2015/0359869 | A1 | 12/2015 | Markham |

FOREIGN PATENT DOCUMENTS

| | | | |
|---|---|---|---|
| WO | 2002058723 | A2 | 8/2002 |
| WO | WO 2004/063220 | A1 * | 7/2004 |
| WO | WO 2010/118252 | A1 * | 10/2010 |
| WO | WO 2012/021558 | A1 * | 2/2012 |
| WO | 2014028664 | A2 | 2/2014 |
| WO | WO 2016/077580 | A2 * | 5/2016 |

OTHER PUBLICATIONS

Gordy et al. (Cancer Research, AACR 106th Annual Meeting 2015, Abstract 2511).*
Vollmer et al. (Advanced Drug Delivery Reviews, 2009, 195-204).*
Schreurs, et al., Cloning, expression and tissue distribution of the murine homologue of the melanocyte lineage-specific antigen gp100. Melanoma Res. Dec. 1997;7(6):463-70.
Martinez-Esparza, et al., Pigment Cell Research. Pigment Cell Res. Jul. 2006;10(4):229-235.
Mahnke, et al., Targeting of antigens to activated dendritic cells in vivo cures metastatic melanoma in mice. Cancer Res. Aug. 1, 2005;65(15):7007-12.
Finn, et al., Persistence of Transgene Expression Influences CD8+ T-Cell Expansion and Maintenance following Immunization with Recombinant Adenovirus. J Virol. Dec. 2009;83(23):12027-12036.
McGray, et al., Immunotherapy-induced CD8+ T Cells Instigate Immune Suppression in the Tumor. Mol Ther. Jan. 2014;22(1):206-218.
Dillman, et al., Cancer stem cell antigen-based vaccines: the preferred strategy for active specific immunotherapy of metastatic melanoma? Expert Opin Biol Ther. May 2013;13(5):643-56.
Alb, et al., Cellular and cytokine-dependent immunosuppressive mechanisms of grm1-transgenic murine melanoma. Cancer Immunol Immunother. Dec. 2012;61(12):2239-49.
Kalli, et al., Comparative analysis of cancer vaccine settings for the selection of an effective protocol in mice. J Transl Med May 12, 2013;11:120.
Castle, et al., Exploiting the mutanome for tumor vaccination. Cancer Res. Mar. 1, 2012;72(5):1081-91.
Hailemichael, et al., Persistent antigen at vaccination sites induces tumor-specific CD8₊ T cell sequestration, dysfunction and deletion. Nat Med. Apr. 2013;19(4):465-72.
Vogelstein, et al., Cancer genome landscapes. Science. Mar. 29, 2013;339(6127):1546-58.
Boca, et al., Patient-oriented gene set analysis for cancer mutation data. Genome Biol. 2010;11(11):R112.

(Continued)

*Primary Examiner* — Sean E Aeder
(74) *Attorney, Agent, or Firm* — Johns Hopkins Technology Ventures

(57) ABSTRACT

Provided herein, in some embodiments, are methods and composition for treating cancer in a subject. The methods may include administering to the subject a nucleic acid encoding MIP3α fused to a cancer antigen, administering to the subject a CpG oligodeoxynucleotide, administering to the subject interferon alpha (IFNα), and administering to the subject 5-aza-2'-deoxycytidine (Aza), in effective amounts to treat the cancer.

1 Claim, 19 Drawing Sheets
Specification includes a Sequence Listing.

(56) References Cited

OTHER PUBLICATIONS

Brown, et al., Neo-antigens predicted by tumor genome meta-analysis correlate with increased patient survival. Genome Res. May 2014;24(5):743-50.
Hwang, et al., A null mutation in the gene encoding a type I interferon receptor component eliminates antiproliferative and antiviral responses to interferons alpha and beta and alters macrophage responses. Proc Natl Acad Sci U S A. Nov. 21, 1995;92(24):11284-8.
Gordy, et al., Fusion of the dendritic cell-targeting chemokine MIP3α to melanoma antigen Gp100 in a therapeutic DNA vaccine significantly enhances immunogenicity and survival in a mouse melanoma model. J Immunother Cancer. 2016;4:96.
Mittendorf, et al., Injecting Hope—A Review of Breast Cancer Vaccines. Oncology (Williston Park). May 2016;30(5):475-81, 485.
Romero, et al., The Human Vaccines Project: A roadmap for cancer vaccine development. Sci Transl Med. Apr. 13, 2016;8(334):334ps9.
Butterfield, Lessons learned from cancer vaccine trials and target antigen choice. Cancer Immunol Immunother. Jul. 2016;65(7):805-12.
Dammeijer, et al., Efficacy of Tumor Vaccines and Cellular Immunotherapies in Non-Small-Cell Lung Cancer: A Systematic Review and Meta-Analysis. J Clin Oncol. Sep. 10, 2016;34(26):3204-12.
Elster, et al., Dendritic cell vaccines: A review of recent developments and their potential pediatric application. Hum Vaccin Immunother. Sep. 2016;12(9):2232-9.
Schneble, et al., Peptide-Based Cancer Vaccine Strategies and Clinical Results. Methods Mol Biol. 2016;1403:797-817.
Luo, et al., Extended protection capabilities of an immature dendritic-cell targeting malaria sporozoite vaccine. Vaccine. Apr. 25, 2017;35(18):2358-2364.
Luo, et al., Fusion of antigen to a dendritic cell targeting chemokine combined with adjuvant yields a malaria DNA vaccine with enhanced protective capabilities. PLoS One Mar. 5, 2014;9(3):e90413.
Neimart-Andersson, et al., Improved immune responses in mice using the novel chitosan adjuvant ViscoGel, with a Haemophilus influenzae type b glycoconjugate vaccine. Vaccine. Nov. 8, 2011;29(48):8965-73.
Dieu, et al., Selective Recruitment of Immature and Mature Dendritic Cells by Distinct Chemokines Expressed in Different Anatomic Sites. J Exp Med. Jul. 20, 1998;188(2):373-386.
Lapteva, et al., CCL5 as an adjuvant for cancer immunotherapy. Expert Opin Biol Ther. May 2010;10(5):725-33.
Loudon, et al., GM-CSF increases mucosal and systemic immunogenicity of an H1N1 influenza DNA vaccine administered into the epidermis of non-human primates PLoS One. Jun. 8, 2010;5(6):e11021.
Nguyen-Hoai, et al., CCL19 as an adjuvant for intradermal gene gun immunization in a Her2/neu mouse tumor model: improved vaccine efficacy and a role for B cells as APC. Cancer Gene Ther. Dec. 2012;19(12):880-7.
Micheva-Viteva, et al., High-throughput screening uncovers a compound that activates latent HIV-1 and acts cooperatively with a histone deacetylase (HDAC) inhibitor. J Biol Chem. Jun. 17, 2011;286(24):21083-91.
Rodriguez, et al., IL-12 and GM-CSF in DNA/MVA immunizations against HIV-1 CRF12_BF Nef induced T-cell responses with an enhanced magnitude, breadth and quality. PLoS One. 2012;7(5):e37801.
Biragyn, et al., Chemokine receptor-mediated delivery directs self-tumor antigen efficiently into the class II processing pathway in vitro and induces protective immunity in vivo. Blood. Oct. 1, 2004;104(7):1961-9.
Biragyn, et al., Tumor-Associated Embryonic Antigen-Expressing Vaccines that Target CCR6 Elicit Potent CD8+ T Cell-Mediated Protective and Therapeutic Antitumor Immunity. J Immunol Jul. 15, 2007;179(2):1381-1388.
Ouyang, et al., Regulation and functions of the IL-10 family of cytokines in inflammation and disease. Annu Rev Immunol. 2011;29:71-109.
Sanlorenzo, et al., Role of interferon in melanoma: old hopes and new perspectives. Expert Opin Biol Ther. Apr. 2017;17(4):475-483.
Kubo, et al., Interferon-beta therapy for malignant melanoma: the dose is crucial for inhibition of proliferation and induction of apoptosis of melanoma cells. Arch Dermatol Res. Jul. 2008;300(6):297-301.
Basham, et al., Interferon increases HLA synthesis in melanoma cells: interferon-resistant and -sensitive cell lines. Proc Natl Acad Sci U S A. May 1982;79(10):3265-3269.
Paquette, et al., Interferon-alpha and granulocyte-macrophage colony-stimulating factor differentiate peripheral blood monocytes into potent antigen-presenting cells. J Leukoc Biol. Sep. 1998;64(3):358-67.
Mocellin, et al., Interferon alpha adjuvant therapy in patients with high-risk melanoma: a systematic review and meta-analysis. J Natl Cancer Inst. Apr. 7, 2010;102(7):493-501.
Fratta, et al., Epigenetics of melanoma: implications for immune-based therapies. Immunotherapy. Oct. 2013;5(10):1103-16.
Lee, et al., Melanoma epigenetics: novel mechanisms, markers, and medicines. Lab Invest. Aug. 2014;94(8):822-38.
Timp, et al., Cancer as a dysregulated epigenome allowing cellular growth advantage at the expense of the host. Nat Rev Cancer. Jul. 2013;13(7):497-510.
Lucarini, et al., Combining Type I Interferons and 5-Aza-2'-Deoxycitidine to Improve Anti-Tumor Response against Melanoma. J Invest Dermatol. Jan. 2017;137(1):159-169.
Saleh, et al., Improving cancer immunotherapy with DNA methyltransferase inhibitors. Cancer Immunol Immunother. Jul. 2016;65(7):787-96.
Wang, et al., Targeting of the non-mutated tumor antigen HER2/neu to mature dendritic cells induces an integrated immune response that protects against breast cancer in mice. Breast Cancer Res. Mar. 7, 2012;14(2):R39.
Grossmann, et al., Enhancement of the priming efficacy of DNA vaccines encoding dendritic cell-targeted antigens by synergistic toll-like receptor ligands. BMC Immunol. Aug. 3, 2009;10:43.
Hao, et al., Mature dendritic cells pulsed with exosomes stimulate efficient cytotoxic T-lymphocyte responses and antitumour immunity. Immunology. Jan. 2007;120(1):90-102.
Kreiter, et al., Mutant MHC class II epitopes drive therapeutic immune responses to cancer. Nature. Apr. 30, 2015;520(7549):692-6.
Tran, et al., Cancer immunotherapy based on mutation-specific CD4+ T cells in a patient with epithelial cancer. Science. May 9, 2014;344(6184):641-5.
Schumacher, et al., A vaccine targeting mutant IDH1 induces antitumour immunity. Nature. Aug. 21, 2014;512(7514):324-7.
Ruffini, et al., Genetic fusions with viral chemokines target delivery of nonimmunogenic antigen to trigger antitumor mmunity independent of chemotaxis. J Leukoc Biol. Jul. 2004;76(1):77-85.
Kledal, et al., A broad-spectrum chemokine antagonist encoded by Kaposi's sarcoma-associated herpesvirus. Science. Sep. 12, 1997;277(5332):1656-9.
Ott, et al., An immunogenic personal neoantigen vaccine for patients with melanoma. Nature. Jul. 13, 2017;547(7662):217-221.
Hsia, et al., Cytosolic DNA Promotes Signal Transducer and Activator of Transcription 3 (STAT3) Phosphorylation by TANK-binding Kinase 1 (TBK1) to Restrain STAT3 Activity. J Biol Chem. Mar. 31, 2017;292(13):5405-5417.
Sali, et al., Characterization of a Novel Human-Specific STING Agonist that Elicits Antiviral Activity Against Emerging Alphaviruses. PLoS Pathog. Dec. 8, 2015;11(12):e1005324.
Schumacher, et al., Neoantigens in cancer immunotherapy. Science. Apr. 3, 2015;348(6230):69-74.
Rizvi, et al., Cancer immunology. Mutational landscape determines sensitivity to PD-1 blockade in non-small cell lung cancer. Science Apr. 3, 2015;348(6230):124-8.
Yang, et al., Beta-defensins: linking innate and adaptive immunity through dendritic and T cell CCR6. Science. Oct. 15, 1999;286(5439):525-8.
Schiavo, et al., Chemokine receptor targeting efficiently directs antigens to MHC class I pathways and elicits antigen-specific CD8+ T-cell responses. Blood. Jun. 15, 2006;107(12):4597-605.

(56) References Cited

OTHER PUBLICATIONS

Ananth, et al., Surgical Stress Abrogates Pre-Existing Protective T Cell Mediated Anti-Tumor Immunity Leading to Postoperative Cancer Recurrence. PLoS One May 19, 2016;11(5):e0155947.

Pilon-Thomas, et al., Immunostimulatory effects of CpG-ODN upon dendritic cell-based immunotherapy in a murine melanoma model. J Immunother. Jul.-Aug. 2006;29(4):381-7.

Zhu, et al., Synergistic innate and adaptive immune response to combination immunotherapy with anti-tumor antigen antibodies and extended serum half-life IL-2. Cancer Cell. Apr. 13, 2015;27(4):489-501.

Moynihan, et al., Eradication of large established tumors in mice by combination immunotherapy that engages innate and adaptive immune responses. Nat Med. Dec. 2016;22(12):1402-1410.

Hodi, Well-defined melanoma antigens as progression markers for melanoma: insights into differential expression and host response based on stage. Clin Cancer Res. Feb. 1, 2006;12(3 Pt 1):673-8.

Lu, et al., Cancer immunotherapy targeting neoantigens. Seminars in Immunology. Feb. 2016;28(1):22-27.

Hartmann, et al., Rational design of new CpG oligonucleotides that combine B cell activation with high IFN-alpha induction in plasmacytoid dendritic cells. Eur J Immunol. Jun. 2003;33(6):1633-41.

Marshall, et al., Identification of a novel CpG DNA class and motif that optimally stimulate B cell and plasmacytoid dendritic cell functions. J Leukoc Biol. Jun. 2003;73(6):781-92.

Rothenfusser, et al., Plasmacytoid dendritic cells: the key to CpG. Hum Immunol. Dec. 2002;63(12):1111-9.

Verthelyi, et al., Human peripheral blood cells differentially recognize and respond to two distinct CPG motifs. J Immunol. Feb. 15, 2001;166(4):2372-7.

Velculescu, et al., Analysing uncharted transcriptomes with SAGE. Trends Genet. Oct. 2000;16(10):423-5.

Segal, et al., Epitope landscape in breast and colorectal cancer. Cancer Res. Feb. 1, 2008;68(3):889-92.

Bardelli, et al., Mutational analysis of gene families in human cancer. Curr Opin Genet Dev. Feb. 2005;15(1):5-12.

Agnandji, et al., First results of phase 3 trial of RTS,S/AS01 malaria vaccine in African children. N Engl J Med. Nov. 17, 2011;365(20):1863-75.

Verdegaal, et al., Neoantigen landscape dynamics during human melanoma-T cell interactions. Nature. Aug. 4, 2016;536(7614):91-5.

Lennerz, et al., The response of autologous T cells to a human melanoma is dominated by mutated neoantigens. Proc Natl Acad Sci U S A. Nov. 1, 2005;102(44):16013-8.

Ward, et al., The Role of Neoantigens in Naturally Occurring and Therapeutically Induced Immune Responses to Cancer. Adv Immunol. 2016;130:25-74.

Yarchoan, et al., Targeting neoantigens to augment antitumour immunity. Nat Rev Cancer. Apr. 2017;17(4):209-222.

Gubin, et al., Tumor neoantigens: building a framework for personalized cancer immunotherapy. J Clin Invest. Sep. 2015;125(9):3413-21.

Wolfel, et al., A p16INK4a-insensitive CDK4 mutant targeted by cytolytic T lymphocytes in a human melanoma. Science. Sep. 1, 1995;269(5228):1281-4.

Gordy, et al., Anti-IL-10-mediated Enhancement of Antitumor Efficacy of a Dendritic Cell-targeting MIP3α-gp100 Vaccine in the B16F10 Mouse Melanoma Model Is Dependent on Type I Interferons. J Immunother. May 2018;41(4):181-189.

Patel, et al., Targeting gp100 and TRP-2 with a DNA vaccine: Incorporating T cell epitopes with a human IgG1 antibody induces potent T cell responses that are associated with favourable clinical outcome in a phase I/II trial. Oncoimmunology. Feb. 22, 2018;7(6):e1433516.

Mendiratta, et al., Therapeutic tumor immunity induced by polyimmunization with melanoma antigens gp100 and TRP-2. Cancer Res. Feb. 1, 2001;61(3):859-63.

Yamano, et al., Enhancement of immunity by a DNA melanoma vaccine against TRP2 with CCL21 as an adjuvant. Mol Ther. Jan. 2006;13(1):194-202.

Xiang, et al., An autologous oral DNA vaccine protects against murine melanoma. Proc Natl Acad Sci USA. May 2000;97(10):5492-5497.

Huang, et al., Antibody responses to melanoma/melanocyte autoantigens in melanoma patients. J Invest Dermatol. Oct. 1998;111(4):662-7.

Qiu, et al., CpG oligodeoxynucleotides augment antitumor efficacy of folate receptor a based DNA vaccine. Oncol Rep. Jun. 2017;37(6):3441-3448.

Suschak, et al., Advancements in DNA vaccine vectors, non-mechanical delivery methods, and molecular adjuvants to increase immunogenicity. Hum Vaccin Immunother. Dec. 2, 2017;13(12):2837-2848.

Yang, et al., DNA vaccine for cancer immunotherapy. Hum Vaccin Immunother. 2014;10(11):3153-64.

* cited by examiner

METHODS AND COMPOSITIONS FOR TREATING CANCER

RELATED APPLICATION

This application claims the benefit under 35 U.S.C. § 119(e) of U.S. provisional application No. 62/576,986, filed Oct. 25, 2017, which is incorporated by reference herein in its entirety.

BACKGROUND

Despite progress in treating and preventing cancer, there is a continued need for improved treatments for many kinds of cancer, such as melanoma. Melanoma is particularly aggressive, and both the incidence of and mortality from invasive melanoma in the United States have been rising during the past few decades. Melanoma treatments have failed, especially at late stages, because these melanomas are able to escape the effect of treatment. Mutations can arise in tumor proteins targeted by the immune system, and mechanisms of immune tolerance can downregulate the immune response to tumor antigens. Current therapies to counteract such tolerance mechanisms are not successful in the majority of patients to date.

SUMMARY

Provided herein, in some aspects, is therapeutic platform for the targeted treatment of various types of cancer, for example, melanoma. The DNA-based immunogenic compositions (e.g., vaccine compositions) and methods of the present disclosure combine, in some embodiments, (a) a DNA construct encoding a fusion protein that targets a (one or more) cancer antigen to immature dendritic cells, which initiate a robust anti-tumor response, (b) CpG oligodeoxynucleotide adjuvant, (c) interferon alpha (IFNα), and (d) 5-aza-2'-deoxycytidine (Aza/decitabine (DACOGEN®)). Surprisingly, this specific combination of agents produces a synergistic effect in test subjects (see, e.g., FIG. 2B).

Thus, the present disclosure provides, in some aspects, methods that comprise administering to a subject diagnosed with cancer a nucleic acid encoding a molecule that binds to CCR6 on immature dendritic cells (e.g., macrophage inflammatory protein-3 alpha (MIP3α)) fused to a cancer antigen (e.g., a neoantigen), administering to the subject CpG oligodeoxynucleotide (CpG ODN) adjuvant, administering to the subject interferon alpha (IFNα), and administering to the subject 5-aza-2'-deoxycytidine (Aza), in effective amounts to induce an immune response in the subject. In some embodiments, each of the forgoing agents is administered separately, while in other embodiments, at least two of the forgoing agents are formulated as a single immunogenic composition. For example, the nucleic acid encoding the fusion protein may be formulated with (e.g., combined with) the CpG ODN and/or the IFNα may be formulated with the Aza.

In some embodiments, the cancer antigen is a melanoma antigen. For example, the cancer antigen may be a neoantigen identified in a subject diagnosed with melanoma.

Also provided herein are composition and kits for treating cancer, such as melanoma.

BRIEF DESCRIPTION OF THE DRAWINGS

(FIG. 1A) Linear representations of expressed immunogenic nucleic acid construct sequences within the plasmid. mMIP3α is full length and functional protein. D-mMIP3a contains a C6S mutation that renders MIP3α ineffective at targeting dendritic cells. "Sp" refers to a 14 amino acid spacer sequence. "Tag" refers to a 29 amino acid region including standard myc and histidine tags. Upstream of the construct is a secretion signal sequence from the mouse IP10 gene. For FIGS. 1B-1F, MGpTrp2 refers to an immunogenic nucleic acid construct encoding MIP3α, Gp100, and Trp2. Mice were challenged at day 0 with $5 \times 10^4$ B16F10 cells and vaccinated on days 5, 12, and 19 with 50 µg plasmid. (FIG. 1B) Tumor size at day 19 post challenge and (FIG. 1C) tumor growth time course from day 0 to day 21 comparing phosphate buffered saline (PBS) control, D-MIP3α-GpTrp2, and MIP3α-GpTrp2. (FIG. 1D) Tumor size at day 19 post challenge and (FIG. 1E) tumor growth time course from day 0 to day 19 comparing PBS control, MGp100, MTrp2, and MGpTrp2. (FIG. 1F) Kaplan-Meier survival analysis of all test groups, assessed by log-rank test. FIGS. 1B-1F show data combined from two to four independent experiments, n=4-6 mice per group per experiment. Log(2) transformed tumor size data tested for significance by anova with Tukey's multiple comparison test. Tumor growth tested by Area Under the Curve calculations with non-overlapping 95% confidence intervals. Outliers more than two standard deviations from the mean were excluded from the dataset. #$p<0.05$ to negative control; *$p<0.05$ compared to all groups. Error bars denote estimate of standard error of the mean.

(FIG. 2A) Therapy schedule. At day 0 mice were challenged with $5 \times 10^4$ B6F10 cells. The immunogenic nucleic acid construct encoded MIP3α-Gp100-Trp2 and was given at a 50 µg/dose followed by intramuscular (i.m.) electroporation. High dose IFNα (10,000 units) and low dose IFNα (1,000 units) were given intratumorally. Aza was given intraperitoneally (i.p.) at 1 mg/kg. (FIG. 2B) Tumor sizes across groups at day 19 post challenge. PBS alone was excluded due to mice already removed from the group due to death or human euthanasia. Statistical analysis was performed on the log(2) transformed data values by one-way anova with Tukey's multiple comparison test. (FIG. 2C) Tumor size progression from day 0 to day 21. Significance was assessed by non-overlapping 95% confidence intervals of Area Under the Curve calculations. (FIG. 2D) Kaplan-Meier Survival curve of all groups, tested by log-rank test. (FIG. 2B-2D) Combined data from two independent experiments, n=3-8 mice per group per experiment. Outliers more than two standard deviations from the mean were excluded from the dataset. On the graphs, statistical significance (α=0.05) is delineated by: #significant to negative control, *significant to all other groups, ^ significant to all groups except Immunogenic Construct+IFNα. Error bars show estimated standard error of the mean.

(FIG. 3A) Therapy schedule. Immunogenic compositions and therapies are the same as outlined in FIGS. 2A-2D. This figure shows analysis of the late time point only. See FIGS. 4A-4D for analysis of the early time point. (FIGS. 3B-2C) Percentage and tumor-size normalized numbers respectively of CD3+CD8+ tumor infiltrating lymphocytes (TILs) that were successfully stimulated by antigenic peptides. (FIGS. 3D-3E) show the percentage and tumor-size normalized numbers respectively of gated TILs that are CD3+CD4+. (FIGS. 3F-3G) show the percentage and tumor-size normalized numbers respectively of gated TILs that are CD3+CD8+. (FIGS. 3H-3I) show the scatterplots and correlations of mice from all groups comparing gated TILs that were CD3⁺CD4⁺ or CD3⁺CD8⁺ respectively to measured tumor size. All panels represent two to three independent experiments with n=3-4 mice per group per experiment. (FIGS. 3B-3G) were assessed by one-way Anova with Tukey's multiple comparison test. Significance was annotated by bars between two groups or by an asterisk where the group is significantly different from all other groups. (FIGS. 3H-3I) were tested by simple linear regression, with $R^2$ and p values noted in the panel. Error bars denote estimate for the standard error of the mean.

(FIG. 4A) Percentage of and (FIG. 4B) tumor-size normalized numbers of CD3⁺CD8⁺ TILs that were IFNγ and TNFα double positive after stimulation with antigenic peptides. (FIG. 4C) Percentage of and (FIG. 4D) tumor size normalized numbers of gated TILs that were CD3⁺CD8⁺. Data represented one experiment of n=3-4 mice per group. Significance tested by one-way Anova with Tukey's multiple comparisons test, with significance noted by bars between groups. Error bars are representative of estimate of the standard error of the mean.

(FIG. 5A) Outlines the early and late time point therapy schedules. For analysis, $\Delta Ct$ is calculated by subtracting the gene of interest Ct value from housekeeping gene GAPDH for each sample. $\Delta\Delta Ct$ is calculated by subtracting $\Delta Ct$ values from gene of interest to the $\Delta Ct$ value of either negative control at the early time point or vaccine-only at the late time point. (FIGS. 5B and 5D) show the overall correlation between Mx1–$\Delta\Delta Ct$ values and tumor size at early (FIG. 5B) and late (FIG. 5D) time points. (FIGS. 5C and 5E) show the comparison across groups of Mx1–$\Delta\Delta Ct$ values at the early and late time points respectively. The data represent two independent experiments, n=3-5 mice per group per experiment. Scatterplots were tested by simple linear regression, with $R^2$ and p values noted on the graphs. Grouped analyses were tested by Anova with Tukey's multiple comparisons test, with significant comparisons marked by bars. Error bars denote estimate of the standard error of the mean.

(FIG. 6A) Tumor Sizes at day 19 post challenge. Data were tested by one-way Anova with Tukey's multiple comparison test. (FIG. 6B) Tumor growth time course through day 21 post challenge. Area Under the Curve statistics were calculated, and interactions were considered significant if 95% confidence intervals did not overlap. (FIG. 6C) Kaplan-Meier survival curve as assessed by log-rank test. Panels A-C show combined data from two independent experiments, n=3-7 mice per group per experiment. Statistical significance designated by bars between groups, α=0.05. Error bars Error bars show estimated standard error of the mean.

(FIG. 7A) Percent survival at indicated days post challenge. (FIG. 7B) Tumor size (mm²) at indicated days post challenge.

DETAILED DESCRIPTION

Figure 1A:
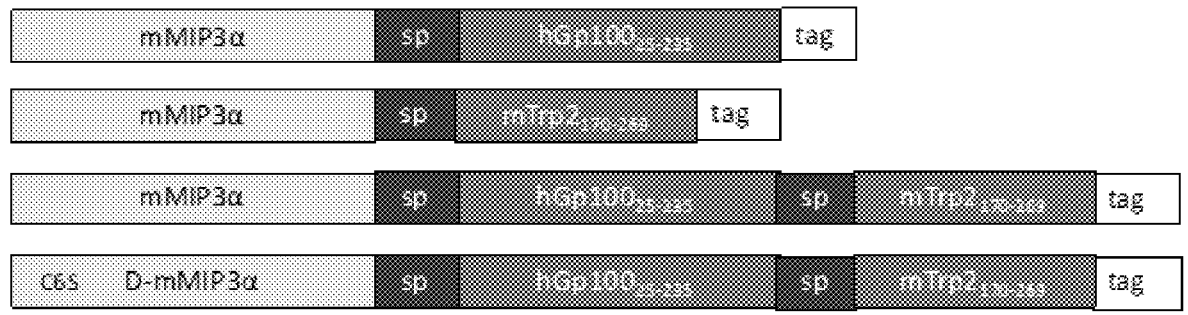
FIGS. 1A-1F: Immunogenic Composition/Therapy Comparisons.

Some aspects of the present disclosure provide cancer vaccination/treatment methods, comprising administering to a subject diagnosed with cancer a nucleic acid (e.g., a DNA or RNA, optionally codon-optimized for human use) encoding a molecule that binds to CCR6 on immature dendritic cells (e.g., macrophage inflammatory protein-3 alpha (MIP3α)) fused to a cancer antigen (referred to as an immunogenic nucleic acid construct), administering to the subject CpG oligodeoxynucleotide (CpG ODN) adjuvant, administering to the subject interferon alpha (IFNα), and/or administering to the subject 5-aza-2'-deoxycytidine (Aza), in effective amounts to induce an immune response in the subject.

Dendritic Cell Targeting Molecules

In some embodiments, an immunogenic nucleic acid construct of the present disclosure encodes a molecule that binds to immature dendritic cells, e.g., to CCR6 located on immature dendritic cells. A dendritic cell is an immune cell that processes antigen material and presents the processed antigenic material to T and B lymphocytes. Thus, a dendritic cell is an antigen-presenting cell. Examples of dendritic cells include myeloid dendritic cells, plasmacytoid dendritic cells, and immature dendritic cells. Dendritic cells (e.g., immature dendritic cells), in some instance, express chemokine receptor molecules such as CCR1, CCR2, CCR5, CCR6, and CXCR1. CCR6, for example, interacts with (e.g., binds to) the chemokine MIP3α. As other examples, the receptors CCR5 and CCR1 interact with (e.g., bind to) chemokine CCL5/RANTES, and the receptors CCR1, CCR4, and CCR5 interacts with (e.g., binds to) the chemokine CCL3/MIP-1α. Thus, in some embodiments, an immunogenic nucleic acid construct encodes MIP3α, CCL5/RANTES, and/or CCL3/MIP-1α, or other molecule that exhibits chemotactic activity toward dendritic cells, fused to a cancer antigen. CCR6, for example, also interacts with (e.g., binds to) other ligands, such as the human β-defensins (e.g., human β-defensin 1 and human β-defensin 2), which exhibit chemotactic activity towards dendritic cells. Thus, in some embodiments, an immunogenic nucleic acid construct encodes a human β-defensin fused to a cancer antigen. Other immature dendritic cell targeting molecules (molecules that exhibit chemotactic activity towards dendritic cells) may be fused to a cancer antigen as provided herein.

Signal Sequence

The immunogenic nucleic acid constructs of the present disclosure, in some embodiments, include a signal sequence encoding a signal peptide. A signal peptide is a short (e.g., ~15-30 amino acid) peptide located at the N-terminal of a protein, functioning to prompt a cell to translocate a cell to the cell membrane. Any signal sequence (encoding a signal peptide) may be used as provided herein. In some embodiments, the signal sequence is a mammalian signal sequence.

In some embodiments, the signal sequence is a human signal sequence. Non-limiting examples of signal peptides that may be encoded by a signal sequence are provided as SEQ ID NOS: 21-26.

Cancer Antigens

A cancer antigen is a molecule (e.g., protein) (a) expressed specifically by a cancer cell and not expressed by non-cancerous cells or (b) overexpressed by a cancer cell and expressed at low levels in some non-cancerous cells, and that induces an immune response, e.g., the production of antibodies or cytotoxic T cells. Non-limiting examples of caner antigens include HER2, BRCA1, prostate-specific membrane antigen (PSMA), MART-1/MelanA, prostatic serum antigen (PSA), squamous cell carcinoma antigen (SCCA), ovarian cancer antigen (OCA), pancreas cancer associated antigen (PaA), MUC-1, MUC-2, MUC-3, MUC-18, carcino-embryonic antigen (CEA), polymorphic epithelial mucin (PEM), Thomsen-Friedenreich (T) antigen, gp100, tyrosinase, TRP-1, TRP-2, NY-ESO-1, CDK-4, b-catenin, MUM-1, Caspase-8, KIAA0205, HPVE7, SART-1, SART-2, PRAME, BAGE-1, DAGE-1, RAGE-1, NAG, TAG-72, CA125, mutated p21ras, mutated p53, HPV16 E7, RCC-3.1.3, MAGE-1, MAGE-2, MAGE-3, MAGE-4, MAGE-11, GAGE-I, GAGE-6, GD2, GD3, GM2, TF, sTn, gp75, EBV-LMP 1, EBV-LMP 2, HPV-F4, HPV-F6, HPV-F7, alpha-fetoprotein (AFP), CO17-1A, GA733, gp72, p-HCG, gp43, HSP-70, p17 mel, HSP-70, gp43, HMW, HOJ-1, HOM-MEL-55, NY-COL-2, HOM-HD-397, HOM-RCC-1.14, HOM-HD-21, HOM-NSCLC-11, HOM-MEL-2.4, HOM-TES-11, melanoma gangliosides, TAG-72, prostatic acid phosphatase, protein MZ2-E, folate-binding-protein LK26, truncated epidermal growth factor receptor (EGFR), GM-2 and GD-2 gangliosides, polymorphic epithelial mucin, folate-binding protein LK26, pancreatic oncofetal antigen, cancer antigen 15-3, cancer antigen 19-9, cancer antigen 549, and/or cancer antigen 195.

In some embodiments, the cancer antigen is a melanoma antigen (an antigen expressed by melanoma cells). Non-limiting examples of melanoma antigens include gp100, gp75 (TRP-1), MelanA/MART-1, TRP-2, MAGE family members (e.g., MAGE-1, MAGE-2, MAGE-3, MAGE-4, MAGE-11), GAGE family members (e.g., GAGE-I and GAGE-6), BAGE family members, NY-ESO-1, MUM-1, b-catenin, CDK4, p15, and D-1, SSX2 (see also Hodi SF Clinical Cancer Research, 2006; 12(3): 673-678, incorporated herein by reference). In some embodiments, the melanoma antigen is gp100. In some embodiments, the melanoma antigen is Trp2.

In some embodiments, the cancer antigen is a neoantigen. Neoantigens are antigens encoded by tumor-specific mutated genes. This class of tumor-specific neoantigens arise via mutations that alter amino acid coding sequences (non-synonymous somatic mutations). Some of these mutated peptides can be expressed, processed and presented on the cell surface, and subsequently recognized by T cells. Because normal tissues do not possess these somatic mutations, neoantigen-specific T cells are not subject to central and peripheral tolerance, and also lack the ability to induce normal tissue destruction. As a result, neoantigens appear to represent ideal targets for T cell-based cancer immunotherapy (see Lu Y et al. Seminars in Immunology, 2016; 28(1): 2-27, incorporated herein by reference). Approaches to identifying T cell neoantigens are known. The majority of the neoantigen-reactive T cells recognized unique mutations not shared between cancer patients. Most of the unique neoantigens were identified by cDNA library screening in the past two decades. In this approach, cDNA library and MHC molecules were over-expressed in cell lines, and then co-cultured with T cells to identify antigens that could induce the T cell activation, measured by cytokine secretion or 4-1BB up-regulation (see Lu Y et al. 2016). A list of published neoantigens is provided in Table 1, any one of which may be used as provided herein. Other approaches to identifying T cell neoantigens, such as next-generation sequencing techniques, may also be used as provided herein.

TABLE 1

Published Human Neoantigens

| Cancer type | Year | Mutated gene name | Approach | Source of T cells |
|---|---|---|---|---|
| Melanoma | 1995 | CDK4 | cDNA library | PBL |
| Melanoma | 1995 | MUM1 | cDNA library | PBL |
| Melanoma | 1996 | CTNNB1 | cDNA library | TIL |
| Melanoma | 1999 | CDC27 | cDNA library | TIL |
| Melanoma | 1999 | TRAPPC1 | cDNA library | PBL |
| Melanoma | 1999 | TPI | Chromatographic purification | TIL |
| Melanoma | 2000 | ASCC3 | cDNA library | PBL |
| Melanoma | 2001 | HHAT | cDNA library | TIL |
| Melanoma | 2002 | FN1 | cDNA library | TIL |
| Melanoma | 2002 | OS-9 | cDNA library | PBL |
| Melanoma | 2003 | PTPRK | cDNA library | TIL |
| Melanoma | 2004 | CDKN2A**, HLA-A11 | cDNA library | TIL |
| Melanoma | 2005 | GAS7, GAPDH | cDNA library | TIL |
| Melanoma | 2005 | SIRT2, GPNMB, SNRP116, RBAF600, SNRPD1 | cDNA library | PBL |
| Melanoma | 2005 | Prdx5 | cDNA library | PBL |
| Melanoma | 2011 | CLPP | cDNA library | TIL |
| Melanoma | 2013 | PPP1R3B | cDNA library | TIL |
| Lung cancer | 1998 | EF2 | Chromatographic purification | PBL |
| Lung cancer | 2001 | ACTN4 | cDNA library | TIL |
| Lung cancer | 2001 | ME1 | cDNA library | PBL |
| Lung Cancer | 2006 | NF-YC | cDNA library | draining lymph node |
| Renal cancer | 1996 | HLA-A2 | cDNA library | PBL |
| Renal cancer | 1999 | HSP70-2 | cDNA library | TIL |
| Renal cancer | 2005 | KIAA1440 | cDNA library | PBL |
| HNSCC | 1997 | CASP8 | cDNA library | PBL |

TIL: tumor infiltrating lymphocytes; PBL: peripheral blood lymphocytes; HNSCC: Head and neck squamous cell carcinoma.

In some embodiments, an immunogenic nucleic acid construct encodes more than one cancer antigen. Thus, in some embodiments, the nucleic acid encodes MIP3α fused to two cancer antigens. In some embodiments, an immunogenic nucleic acid construct encodes one, two, three, four, or five different cancer antigens. In some embodiments, an immunogenic nucleic acid construct encodes one, two, three, four, or five copies of the same cancer antigen.

In some embodiments, an immunogenic nucleic acid construct encodes a dendritic cell targeting molecule (e.g., MIP3α) fused to gp100 and Trp2.

Immunomodulatory Agents

An immunogenic nucleic acid construct of the present disclosure, in some embodiments, is administered to a subject in combination with an immunomodulatory agent.

An immunomodulatory agent is a substance that stimulates or suppresses the immune system. An adjuvant, discussed below, is a type of immunomodulatory agent that stimulates the immune system in response to an antigen. Other non-limiting examples of immunomodulatory agents include DNA methylation inhibitors, histone deacetylase (HDAC) inhibitors, immune checkpoint blockade inhibitors (e.g., anti-PD-1 antibodies, anti-PD-1L antibodies, and/or anti-CTLA-4 antibodies), inhibitors of regulatory T cells, inhibitors of monocyte-derived suppressor cells, and/or components of the Stimulator of Interferon Genes (STING) pathway.

In some embodiments, the immunomodulatory agent is a derivative of 5'-azaycytidine. For example, the immunomodulatory agent may be 5-aza-2'-deoxycytidine (Aza):

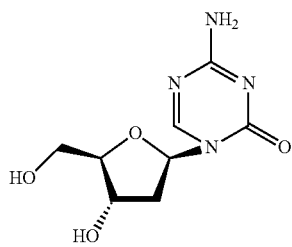

Aza is an inhibitor of DNA methyltransferase, and enhances apoptosis induced by HDAC (histone deacetylase) inhibitors. In some embodiments, a method or composition of the present disclosure includes both Aza and a HDAC inhibitor. Aza also sustains expression of interferon regulated genes, the expression of which would otherwise be inhibited by DNA methylation. In some embodiments, a method or composition of the present disclosure includes both Aza and a Type I interferon (e.g., IFNα or IFNβ).

An immunomodulatory agent (e.g., Aza), in some embodiments, is co-formulated with an immunogenic nucleic acid construct (e.g., encoding MIP-3α fused to a cancer antigen), an adjuvant (e.g., CpG ODN), and/or an interferon (e.g., IFNα)). Two agents are considered co-formulated if they are present in the same composition (e.g., the same solution). In some embodiments, immunomodulatory agent (e.g., Aza) is co-formulated with an immunogenic nucleic acid construct (e.g., encoding MIP-3α fused to a cancer antigen). In some embodiments, immunomodulatory agent (e.g., Aza) is co-formulated with an adjuvant (e.g., CpG ODN). In some embodiments, immunomodulatory agent (e.g., Aza) is co-formulated with an interferon (IFNα). In some embodiments, immunomodulatory agent (e.g., Aza) is administered before (e.g., 1 min-60 min before, 1 hr-24 hr before, 1-5 days before, etc.), after (e.g., 1 min-60 min after, 1 hr-24 hr after, 1-5 days after, etc.), or at the same time (e.g., co-formulated) as an immunogenic nucleic acid construct (e.g., encoding MIP-3α fused to a cancer antigen). In some embodiments, immunomodulatory agent (e.g., Aza) is administered before, after, or at the same time as an adjuvant (e.g., CpG ODN). In some embodiments, immunomodulatory agent (e.g., Aza) is administered before, after, or at the same time as an interferon (e.g., IFNα).

Adjuvants

An immunogenic nucleic acid construct of the present disclosure, in some embodiments, is administered to a subject in combination with an adjuvant. In some embodiments, the adjuvant is a CpG oligodeoxynucleotide (CpG ODN).

CpG ODNs are short synthetic single-stranded DNA molecules containing unmethylated CpG dinucleotides in particular sequence contexts (CpG motifs). CpG ODNs include, in some embodiments, a partially or completely phosphorothioated (PS) backbone.

Three major classes of stimulatory CpG ODNs have been identified based on structural characteristics and activity on human peripheral blood mononuclear cells, in particular B cells and plasmacytoid dendritic cells. These three classes are Class A (Type D), Class B (Type K) and Class C. See, e.g., Hartmann G. et al. Eur J Immunol. 2003; 33:1633-41; Marshall J et al. J Leukoc Biol. 2003; 73:781-92; Rothenfusser S. et al. Hum Immunol. 2002; 63:1111-9; and Verthelyi D. et al. J Immunol. 2001; 166:2372-7.

Class A CpG ODNs are characterized by a PO central CpG-containing palindromic motif and a PS-modified 3' poly-G string. They induce high IFN-α production from pDCs but are weak stimulators of TLR9-dependent NF-κB signaling and pro-inflammatory cytokine (e.g. IL-6) production. In some embodiments, the CpG ODN is a Class A CpG ODN. Non-limiting examples of Class A CpG ODNs include ODN 2216 and ODN 2336 (InvivoGen®).

Class B CpG ODNs contain a full PS backbone with one or more CpG dinucleotides. They strongly activate B cells and TLR9-dependent NF-κB signaling but weakly stimulate IFN-α secretion. In some embodiments, the CpG ODN is a Class B CpG ODN. Non-limiting examples of Class B CpG ODNs include ODN 2006, ODN BW006, and ODN D-SL01 (InvivoGen®).

Class C CpG ODNs combine features of both classes A and B. They contain a complete PS backbone and a CpG-containing palindromic motif. C-Class CpG ODNs induce strong IFN-α production from plasmacytoid dendritic cells as well as B cell stimulation. In some embodiments, the CpG ODN is a Class C CpG ODN. Non-limiting examples of Class C CpG ODNs include ODN 2395, ODN M362, and ODN SL03 (InvivoGen®). In some embodiments, the CpG ODN is ODN 2395 (InvivoGen®).

An adjuvant, in some embodiments, is co-formulated with an immunogenic nucleic acid construct (e.g., encoding MIP-3α fused to a cancer antigen), an interferon (e.g., IFNα), and/or an immunomodulatory agent (e.g., 5-aza-2'-deoxycytidine (Aza)). In some embodiments, an adjuvant (e.g., CpG ODN) is co-formulated with an immunogenic nucleic acid construct (e.g., encoding MIP-3α fused to a cancer antigen). In some embodiments, an adjuvant (e.g., CpG ODN) is co-formulated with an interferon (e.g., IFNα). In some embodiments, an adjuvant (e.g., CpG ODN) is co-formulated with an immunomodulatory agent (e.g. Aza).

In some embodiments, an adjuvant (e.g., CpG ODN) is administered before (e.g., 1 min-60 min before, 1 hr-24 hr before, 1-5 days before, etc.), after (e.g., 1 min-60 min after, 1 hr-24 hr after, 1-5 days after, etc.), or at the same time (e.g., co-formulated) as an immunogenic nucleic acid construct (e.g., encoding MIP-3α fused to a cancer antigen). In some embodiments, an adjuvant (e.g., CpG ODN) is administered before, after, or at the same time as an interferon (e.g., IFNα). In some embodiments, an adjuvant (e.g., CpG ODN) is administered before, after, or at the same time as an immunomodulatory agent (e.g. Aza).

Interferon Alpha

An immunogenic nucleic acid construct of the present disclosure, in some embodiments, is administered to a subject in combination with interferon alpha (IFNα). In some embodiments, an immunogenic nucleic acid construct is administered to a subject before (e.g., 1-5 days before), after (e.g., 1-5 days after), or at the same time (e.g., on the same day or co-formulated) IFNα is administered to the subject.

IFNα (also referred to as INN or HuIFN-alpha-Le (Multiferon®)) is available as a pharmaceutical drug composed of natural interferon alpha (IFNα) obtained from the leukocyte fraction of human blood following induction with Sendai virus. INN contains a mixture of several proteins, all with structural, serological, and functional properties typical for natural interferon alpha (IFNα). The major subtypes identified are IFN-α1, IFN-α2, IFN-α8, IFN-α10, IFN-α14 and IFN-α21. Of these, IFN-α2 and IFN-α14 are glycosylated. The IFN-α content is expressed in International Units per milliliter, and the drug product is formulated in isotonic phosphate buffer solution at pH=7.2, and supplemented with human albumin at 1.5 mg/ml. The albumin used is a medicinal product approved in several countries, and is indicated for subcutaneous injection therapy. Non-limiting examples of IFNs for administration as provided herein include IFNα subtypes IFNα1, IFNα2, IFNα4, IFNα5, IFNα6, IFNα7, IFNα8, IFNα10, IFNα13, IFNα14, IFNα16, IFNα17, and IFNα21. Interferon Type I family members, such as IFNβ, may also be administered as provided herein.

An interferon (e.g., IFNα), in some embodiments, is co-formulated with an immunogenic nucleic acid construct (e.g., encoding MIP-3α fused to a cancer antigen), an adjuvant (e.g., CpG ODN), and/or an immunomodulatory agent (e.g., 5-aza-2'-deoxycytidine (Aza)). In some embodiments, an interferon (e.g., IFNα) is co-formulated with an immunogenic nucleic acid construct (e.g., encoding MIP-3α fused to a cancer antigen). In some embodiments, an interferon (e.g., IFNα) is co-formulated with an adjuvant (e.g., CpG ODN). In some embodiments, an interferon (e.g., IFNα) is co-formulated with an immunomodulatory agent (e.g. Aza).

In some embodiments, an interferon (e.g., IFNα) is administered before (e.g., 1 min-60 min before, 1 hr-24 hr before, 1-5 days before, etc.), after (e.g., 1 min-60 min after, 1 hr-24 hr after, 1-5 days after, etc.), or at the same time (e.g., co-formulated) as an immunogenic nucleic acid construct (e.g., encoding MIP-3α fused to a cancer antigen). In some embodiments, an interferon (e.g., IFNα) is administered before, after, or at the same time as an adjuvant (e.g., CpG ODN). In some embodiments, an interferon (e.g., IFNα) is administered before, after, or at the same time as an immunomodulatory agent (e.g. Aza).

Routes of Administration

The compositions of the present disclosure are not limited by routes of administration. For example, any of the substances disclosed herein (e.g., immunogenic nucleic acid construct), adjuvant, interferon, and/or immunomodulatory agent) may be administered intravenously, intratumorally, orally, subcutaneously, or intramuscularly. In some embodiments, an immunogenic nucleic acid construct is administered intravenously. In some embodiments, an immunogenic nucleic acid construct is administered intramuscularly. In some embodiments, an immunogenic nucleic acid construct is administered subcutaneously. In some embodiments, adjuvant is administered intravenously. In some embodiments, adjuvant is administered intramuscularly. In some embodiments, adjuvant is administered subcutaneously. In some embodiments, interferon is administered intravenously. In some embodiments, interferon is administered intramuscularly. In some embodiments, interferon is administered subcutaneously. In some embodiments, an immunomodulatory agent is administered intravenously. In some embodiments, an immunomodulatory agent is administered intramuscularly. In some embodiments, an immunomodulatory agent is administered subcutaneously.

The immunogenic nucleic acid constructs of the present disclosure, in some embodiments, are encoded on a plasmid or a viral vector. For example, the viral vector may be an adenoviral vector or an adeno-associated viral vector. In some embodiments, the immunogenic nucleic acid constructs are formulated in nanoparticle, such as a lipid nanoparticle or liposome.

Therapeutic Effects

In some embodiments, methods of the present disclosure extend survival time of a subject by at least 20% relative to a control, following administration of the effective amounts of the immunogenic nucleic acid construct (e.g., a nucleic acid encoding MIP3α fused to a cancer antigen), adjuvant (e.g., CpG ODN), interferon (e.g., IFNα), and immunomodulatory agent (e.g., Aza). For example, methods of the present disclosure may extend survival time of a subject by at least 25%, at least 30%, at least 35%, at least 40%, at least 35%, at least 40%, at least 45%, at least 50%, at least 55%, at least 60%, at least 65%, at least 70%, at least 75%, at least 80%, at least 85%, at least 90%, or at least 95% relative to a control. In some embodiments, methods of the present disclosure may extend survival time of a subject by 20%-100%, 20%-90%, 20%-80%, 20%-70%, 20%-60%, 20%-50%, 30%-100%, 30%-90%, 30%-80%, 30%-70%, 30%-60%, 30%-50%, 40%-100%, 40%-90%, 40%-80%, 40%-70%, 40%-60%, 40%-50%, 50%-100%, 50%-90%, 50%-80%, 50%-70%, or 50%-60%.

In some embodiments, methods of the present disclosure reduce volume of a tumor in a subject by at least 20% relative to a control, following administration of the effective amounts of the immunogenic nucleic acid construct (e.g., a nucleic acid encoding MIP3α fused to a cancer antigen), adjuvant (e.g., CpG ODN), interferon (e.g., IFNα), and immunomodulatory agent (e.g., Aza). For example, methods of the present disclosure may reduce volume of a tumor by at least 25%, at least 30%, at least 35%, at least 40%, at least 35%, at least 40%, at least 45%, at least 50%, at least 55%, at least 60%, at least 65%, at least 70%, at least 75%, at least 80%, at least 85%, at least 90%, or at least 95% relative to a control. In some embodiments, methods of the present disclosure may reduce volume of a tumor by 20%-100%, 20%-90%, 20%-80%, 20%-70%, 20%-60%, 20%-50%, 30%-100%, 30%-90%, 30%-80%, 30%-70%, 30%-60%, 30%-50%, 40%-100%, 40%-90%, 40%-80%, 40%-70%, 40%-60%, 40%-50%, 50%-100%, 50%-90%, 50%-80%, 50%-70%, or 50%-60%.

A control may be "no immunogenic composition" or an immunogenic composition without one, two, or three of the following agents: adjuvant (e.g., CpG ODN), interferon (e.g., IFNα), and immunomodulatory agent (e.g., Aza).

In some embodiments, the immune response comprises a humoral immune response. The humoral immune response is mediated by antibody molecules that are secreted by plasma cells. Antigen that binds to the B-cell antigen receptor signals B cells and is, at the same time, internalized and processed into peptides that activate armed helper T cells. Signals from the bound antigen and from the helper T cell induce the B cell to proliferate and differentiate into a plasma cell secreting specific antibody. These antibodies protect the host from infection in three main ways: through neutralization, opsonization, or activation of the complement system.

In some embodiments, the immune response comprises a cellular immune response. The cellular immune response is a protective immune process that involves the activation of phagocytes—antigen-sensitized cytotoxic T cells and the release of cytokines and chemokines in response to antigen. Cellular immunity is most effective against cells infected with viruses, intracellular bacteria, fungi and protozoans, and cancerous cells.

The dose/dosage of each of the agents described herein (e.g., immunogenic nucleic acid construct (e.g., a nucleic acid encoding MIP3α fused to a cancer antigen), adjuvant (e.g., CpG ODN), interferon (e.g., IFNα), and/or immunomodulatory agent (e.g., Aza) may vary, for example, depending on the subject (e.g., age, sex, race, etc.), .route of administration, the type of dendritic cell targeting molecule, cancer antigen interferon, and/or immunomodulatory agent, and/or the specific combination of agents used as provided herein.

In some embodiments, the immunogenic nucleic acid construct (e.g., encoding MIP3α fused to a cancer antigen) is administered at a dose of 10 μg to 10 mg. For example, the immunogenic nucleic acid construct may be administered at a dose of 10 μg, 20 μg, 30 μg, 40 μg, 50 μg, 60 μg, 70 μg, 80 μg, 90 μg, 100 μg, 150 μg, 200 μg, 250 μg, 300 μg, 350 μg, 400 μg, 450 μg, 500 μg, 550 μg, 600 μg, 650 μg, 700 μg, 750 μg, 800 μg, 850 μg, 900 μg, 950 μg, 1 mg, 1.1 mg, 1.2 mg, 1.3 mg, 1.4 mg, 1.5 mg, 1.6 mg, 1.7 mg, 1.8 mg, 1.9 mg, 2 mg, 2.5 mg, 3 mg, 3.5 mg, 4 mg, 4.5 mg, 5 mg, 5.5 mg, 6 mg, 6.6 mg, 7 mg, 7.5 mg, 8 mg, 8.5 mg, 9 mg, 9.5 mg, or 10 mg. In some embodiments, the immunogenic nucleic acid construct is administered at a dose of 10 μg to 100 μg, 100 μg to 1 mg, 1 mg to 2 mg, 1 mg to 5 mg, 1 mg to 10 mg, or 5 mg to 10 mg. A single dose may be administered to more than one dose may be administered.

In some embodiments, the interferon (e.g., IFNα) is administered at a dose of 1 million units to 20 million units. For example, the interferon may be administered at a dose of 1 million units, 2 million units, 3 million units, 4 million units, 5 million units, 6 million units, 7 million units, 8 million units, 9 million units, 10 million units, 11 million units, 12 million units, 13 million units, 14 million units, 15 million units, 16 million units, 17 million units, 18 million units, 19 million units, or 20 million units. A high dose of interferon may be higher than 10 million units (e.g., 11, 12, 13, 14, 15, 16, 17, 18, 19, or 20 million units). A low dose of interferon may be 10 million units or lower (e.g., 10, 9, 8, 7, 6, 5, 4, 3, 2, or 1 million units).

In some embodiments, the immunomodulatory agent (e.g., decitabine/5-aza-2'-deoxycytidine (DACOGEN®)) is administered according to one of the following schedules, although other doses/dosages and/or schedules may be used:

15 mg/m$^2$ by continuous IV infusion over 3 hours, repeated every 8 hours for 3 days (135 mg/m$^2$ per cycle). Repeat every 6 weeks.

20 mg/m$^2$ by continuous IV infusion over 1 hour repeated daily for 5 days (100 mg/m$^2$ per cycle). Repeat every 4 weeks.

In some embodiments, the adjuvant (e.g., CpG ODN) is administered at a dose of 0.01 mg/kg to 1 mg/kg. For example, the adjuvant may be administered at a dose of 0.01 mg/kg, 0.02 mg/kg, 0.03 mg/kg, 0.04 mg/kg, 0.05 mg/kg, 0.06 mg/kg, 0.07 mg/kg, 0.08 mg/kg, 0.09 mg/kg, 0.10 mg/kg, 0.20 mg/kg, 0.30 mg/kg, 0.40 mg/kg, 0.50 mg/kg, 0.60 mg/kg, 0.70 mg/kg, 0.80 mg/kg, 0.90 mg/kg, 1.0 mg/kg. In some embodiments, the adjuvant is administered at a dose of 0.01 mg/kg to 0.05 mg/kg, 0.01 to 0.1 mg/kg, or 0.1 mg/kg to 1 mg/kg. In some embodiments, the adjuvant is administered at a dose of 10 μg to 100 mg. For example, the adjuvant may be administered at a dose of 10 μg, 25 μg, 50 μg, 100 μg, 150 μg, 200 μg, 300 μg, 400 μg, 500 μg, 600 μg, 700 μg, 800 μg, 900 μg, 1 mg, 5 mg, 10 mg, 20 mg, 30 mg, 40 mg, 50 mg, 60 mg, 70 mg, 80 mg, 90 mg, or 100 mg. In some embodiments, the adjuvant is administered at a dose of 10 μg to 100 μg, 100 μg to 500 μg, 500 μg to 1 mg, 1 mg to 10 mg, 10 mg to 50 mg, 10 mg to 100 mg, or 50 mg to 100 mg.

Compositions and Kits

Also provided herein are compositions and kits (e.g., used in the methods as provided herein). A composition (e.g., an immunogenic composition) and/or kit, in some embodiments, may comprises an immunogenic nucleic acid construct, adjuvant, interferon, and/or an immunomodulatory agent (e.g., an additional immunomodulatory agent that is not an adjuvant, e.g., not CpG ODN). In some embodiments, a composition and/or kit comprises an immunogenic nucleic acid construct and an adjuvant. In some embodiments, a composition and/or kit comprises an immunogenic nucleic acid construct and an interferon. In some embodiments, a composition and/or kit comprises an immunogenic nucleic acid construct and an immunomodulatory agent. In some embodiments, a composition and/or kit comprises an adjuvant and an interferon. In some embodiments, a composition and/or kit comprises an adjuvant and an immunomodulatory agent. In some embodiments, a composition and/or kit comprises an interferon and an immunomodulatory agent. In some embodiments, a composition and/or kit comprises an immunogenic nucleic acid construct, an adjuvant, and an interferon. In some embodiments, a composition and/or kit comprises an immunogenic nucleic acid construct, an adjuvant, and an immunomodulatory agent. In some embodiments, a composition and/or kit comprises an adjuvant, interferon, and an immunomodulatory agent. In some embodiments, a composition and/or kit comprises an immunogenic nucleic acid construct, an adjuvant, and an interferon, and an immunomodulatory agent.

In some embodiments, a composition and/or kit comprises a pharmaceutically acceptable carrier and/or excipient (e.g., buffer, e.g., normal saline). In some embodiments, one or more of the foregoing agents (e.g., an immunogenic nucleic acid construct, an adjuvant, and an interferon, and/or an immunomodulatory agent) are formulated for intravenous or intramuscular administration.

EXAMPLES

Animals and Tumor Model 5-6 week old female C57BL/6 (H-2b) mice were purchased from Charles River Laboratories (Wilmington, Mass.) and maintained in a pathogen-free micro-isolation facility in accordance with the National Institutes of Health guidelines for the humane use of laboratory animals. B16F10 melanoma cells were cultured from frozen stock for at least three days and no more than ten passages under sterile conditions utilizing complete growth media (Dulbecco's Modified Eagles Medium [DMEM+L-glutamine, L glucose, and sodium pyruvate; Corning™ Cellgro™, Corning, N.Y.]; 10% Fetal Bovine Serum [FBS, Corning™

Corning, N.Y.]; 0.1% gentamycin [Quality Biological, Gaithersburg, Md.]; 2% penicillin/streptomycin [Corning™ Cellgro™, Corning, N.Y.]; and 1% non-essential amino acids [Gibco™, Life Technologies, Carlsbad, Calif.]). Cells were passaged utilizing 0.25% Trypsin (Quality Biological, Gaithersburg, Md.). Prior to challenge, cells were assessed by Gibco™ Trypan Blue solution 0.4% (Life Technologies, Carlsbad, Calif.), ensuring cell viability 95%. 6-8 week old mice were challenged in the left flank subcutaneously with a lethal dose of B16F10 melanoma ($5 \times 10^4$ cells in sterile 1×Hanks Balanced Salt Solution [Gibco™, Life Technologies, Carlsbad, Calif.]). Tumor size was recorded as square mm, representing tumor length×width (opposing axes) measured by calipers every 1-3 days. Mice were kept in survival studies until one of the following occurred: mouse death, tumor diameter eclipsing 20 mm, significant lethargy, or extensive tumor necrosis resulting in excessive bleeding.

Plasmid Design

The original plasmid encoded the MIP3α-hgp100 fusion sequence, where the antigen includes amino acids 25-235 of human gp100. An immunogenic nucleic acid construct encoding mouse MIP3α fused to aforementioned hgp100 and additionally mouse tyrosinase-related protein 2 (Trp2) ranging amino acids 170-269 was created. The region of Trp2 included a 5' spacer region (amino acids MEFN-DAQAPKSLEA (SEQ ID NO: 1)) and was flanked by XbaI restriction sites. This construct was synthesized by Genscript Biotech Corp (Piscataway Township, N.J.) in the pUC57 cloning vector. Using standard cloning techniques, the spacer-Trp2 sequence was cloned from pUC57 to downstream of MIP3α-gp100 and also dMIP3α-gp100 using the XbaI restriction enzyme (New England Biolabs, Ipswich, Mass.) to create MIP3α-Gp100-Trp2 and dMIP3α-Gp100-Trp2 constructs. The MIP3α-Trp2 construct was created by using the following primers [F: 5'-ctcgagagtctcgaagctgggctggt-3' (SEQ ID NO: 2) and R: 5'-ctgttcttctgcggatctctctagagtcg-3' (SEQ ID NO: 3)] to PCR amplify the Trp2 region from the MIP3α-Gp100-Trp2 plasmid, incorporating an xhol restriction site to 5' end of the construct downstream of extant xbal site. PCR amplification was performed using Taq DNA Polymerase with Standard Taq Buffer according to manufacturer's protocol (New England Biolabs, Ipswich, Mass.). The PCR product was inserted into pCR™ 2.1-TOPO® TA Cloning® plasmid according to manufacturer's protocol (Invitrogen™ ThermoFisher Scientific, Waltham, Mass.). Utilizing standard cloning techniques, xbal and xhol enzymes (New England Biolabs, Ipswich, Mass.) were used to clone the Trp2 sequence from the pCR™ 2.1-TOPO® TA Cloning® plasmid into the MIP3α-gp100 plasmid, replacing the gp100 with Trp2 to create a MIP3α-Trp2 construct.

Vaccinations and Therapeutics

Vaccination plasmids were extracted from *E. coli* using Qiagen® (Germantown, Md.) EndoFree® Plasmid Maxi, Mega, and Giga Kits and were diluted with endotoxin-free 1×PBS. DNA purity, quality, and quantity were verified by gel electrophoresis, restriction enzyme analysis, Nanodrop® spectrophotometry, and insert sequencing (JHMI Synthesis and Sequencing Facility, Baltimore, Md.). Mock vaccinations were comprised of endotoxin-free PBS only. DNA injections were administered into the hind leg tibialis muscle. Immediately following injection, the muscle was pulsed using an ECM 830 Electro Square Porator™ with 2-Needle Array™ Electrode (BTX Harvard Apparatus®; Holliston, Mass.) under the following parameters: 106V; 20 ms pulse length; 200 ms pulse interval; 8 total pulses. Vaccinations of 50 µg/dose were delivered at days noted in figure legends. If included in the regimen, 50 µg ODN2395 Type C CpG (Innaxon LPS Biosciences, Tewkesbury, UK) was administered two days after vaccination intramuscularly into vaccinated muscle. Recombinant Mouse Interferon Alpha-A (IFNα, R&D Systems, Inc. Minneapolis, Minn.) administered either intratumorally or intramuscularly as indicated. If intramuscular, it was administered into non-vaccinated leg tibialis muscle. High doses of IFNα were 10,000 units per dose and low doses were 1,000 units per dose. InSolution™ 5-aza-2'-deoxycytidine (Aza, CalBiochem®, MilliporeSigma, Burlington, Mass.) was administered interperitoneally at 1 mg/kg in 50 µl, at approximately 20 µg/mouse.

Extraction of Splenocytes and TILs

Spleen and tumor cell suspensions were prepared by grinding sterile excised tissue between the frosted ends of microscope slides and then passing the tissue through a sterile 70 µM mesh (Westnet, Inc. Canton, Mass.). Splenocytes were processed by lysing red blood cells according to manufacturer's protocol (ACK lysing buffer, Quality Biological, Gaithersburg, Md.) and washing with sterile PBS. For tumor lymphocyte analysis, tumor lysate was washed with sterile PBS, and the mononuclear cell fraction (including TILs) was enriched by Lympholyte®-M Cell Separation Media (Cedarlane®, Burlington, N.C.) according to the manufacturer's protocol. Tissues/cells kept on ice or at 4° C. at all points possible. Single cell suspensions were either stimulated immediately or left at 4° C. overnight.

Intracellular Cytokine Staining and Flow Cytometry

Enriched splenocytes or TILs were seeded onto Falcon® Multiwell 24-well tissue culture treated plates (Corning, Inc.; Corning, N.Y.) at approximately $1 \times 10^6$ cells per well (or all cells if total was less) and stimulated for 3-5 hours at 37° C. with equal concentrations of known immunodominant peptides gp100$_{25-33}$ (KVPRNQDWL (SEQ ID NO: 4); JHU School of Medicine Synthesis & Sequencing Facility; Baltimore, Md.) and Trp2$_{180-188}$ (SVYDFFVWL (SEQ ID NO: 5); Anaspec Inc. Fremont, Calif.) or with control HA peptide (YPYDVPDYA (SEQ ID NO: 6); JHU School of Medicine Synthesis & Sequencing Facility; Baltimore, Md.) for a total of 20 µg of peptide per sample. Peptide(s) were combined with Protein Transport Inhibitor Cocktail and costimulatory anti-CD28 and anti-CD49d agonizing antibodies (eBioscience, Inc. San Diego, Calif.). Assay positive controls were stimulated with Cell Stimulation Cocktail and Protein Transport Inhibitor Cocktail (eBioscience, Inc. San Diego, Calif.). Cells were collected, washed, fixed, permeabilized, and stained using standard laboratory protocols for intracellular staining. Fixation and permeabilization buffers from BD Cytofix/Cytoperm™ Kit (BD Biosciences, San Jose, Calif.) were used. Stains utilized were the following anti-mouse mAbs: PercPCy5.5 conjugated anti-CD3, APC-IFNγ, FITC-CD8, PE-CD4, PECy7-TNFα, (eBioscience, Inc. San Diego, Calif.), FITC-CD8, and Live/Dead Near-IR (Invitrogen by Thermo Fisher Scientific, Carlsbad, Calif.). The Attune™ NxT (Thermo Fisher Scientific, Waltham, Mass.) flow cytometer was utilized. Flow data were analyzed by FlowJo Software (FlowJo, LLC Ashland, Oreg.). Total cell count estimation was back-calculated from volume utilized by cytometer to create a cell concentration value that could be applied to the total volume of sample.

RNA Extraction and qRT-PCR

Mice were sacrificed and portions of tumor weighing less than 100 mg were harvested. Tumor was minced as finely as possible, added to 1 ml Trizol® (Ambion® by Life Technologies, Carlsbad, Calif.), and then homogenized by the Fisher Scientific™ PowerGen 125 (Thermo Fisher Scientific, Waltham, Mass.). RNA was extracted utilizing the manufacturer's protocol and including a 75% ethanol wash step. The pellet was air dried and resuspended in nuclease-free water. The cDNA Reverse Transcription reaction was performed with 1 µg extracted RNA and the High Capacity cDNA Reverse Transcription Kit with random primers (Applied Biosystems™ by Thermo Fisher, Halethorpe, Md.) utilizing the manufacturer's protocol. Real-Time quantitative Reverse Transcription-PCR (qRT-PCR) performed utilizing TaqMan® Gene Expression Master Mix or Fast Advanced Master Mix and TaqMan® Gene Expression Assays (Applied Biosystems™ by Thermo Fisher, Halethorpe, Md.) with probes specific for GAPDH (expression control), Pmel (gp100), Dct (Trp2), MlnA, and Mx1 utilizing manufacturer's protocols. qRT-PCR ran with StepOnePlus™ machine and software (Applied Biosystems™ by Thermo Fisher, Halethorpe, Md.).

Statistics and Data

Tumor size, immunologic, RT-PCR, and flow cytometric analyses were statistically tested by one-way anova with Tukey's multiple comparisons test if multiple groups or by Student's t-test if two groups. Mouse survival studies were statistically tested by the log-rank test. Scatter plots were analyzed by simple linear regression. Tumor time courses were analyzed by Area Under the Curve calculations with 95% confidence intervals (CI), where non-overlapping CI's were considered significantly different. Microsoft® Excel (Microsoft Corp, Redmond, Wash.) was used for database management. Prism 7 (GraphPad Software, Inc. San Diego, Calif.) was utilized for statistical analyses and figure creation. A significance level of $\alpha \leq 0.05$ was set for all experiments.

Figure 1B:
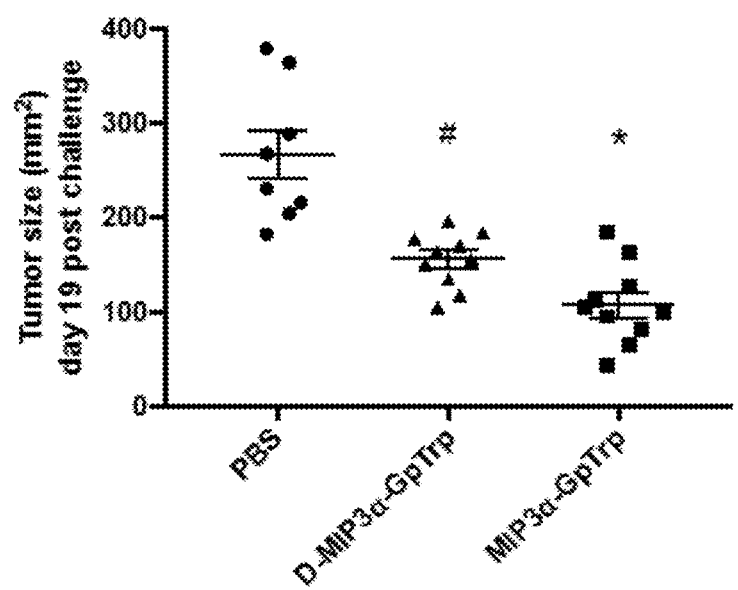
Figure 1C:
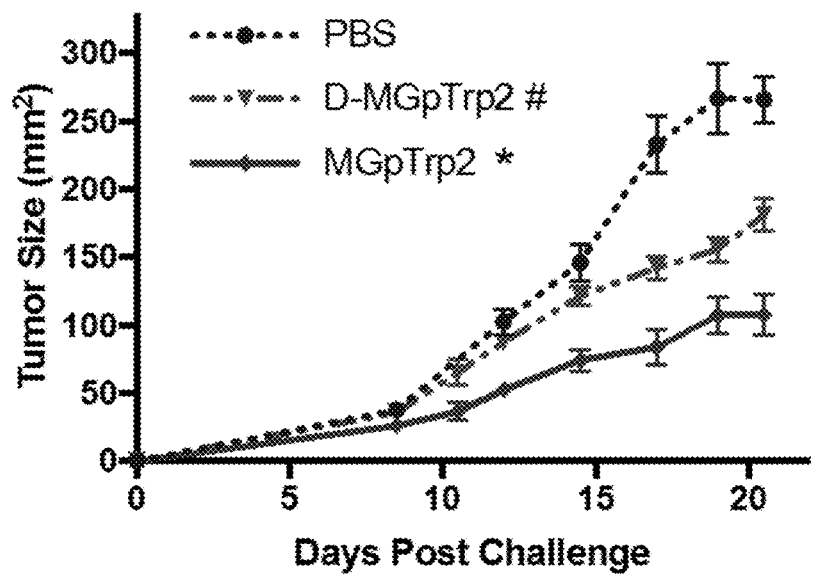
Figure 1D:
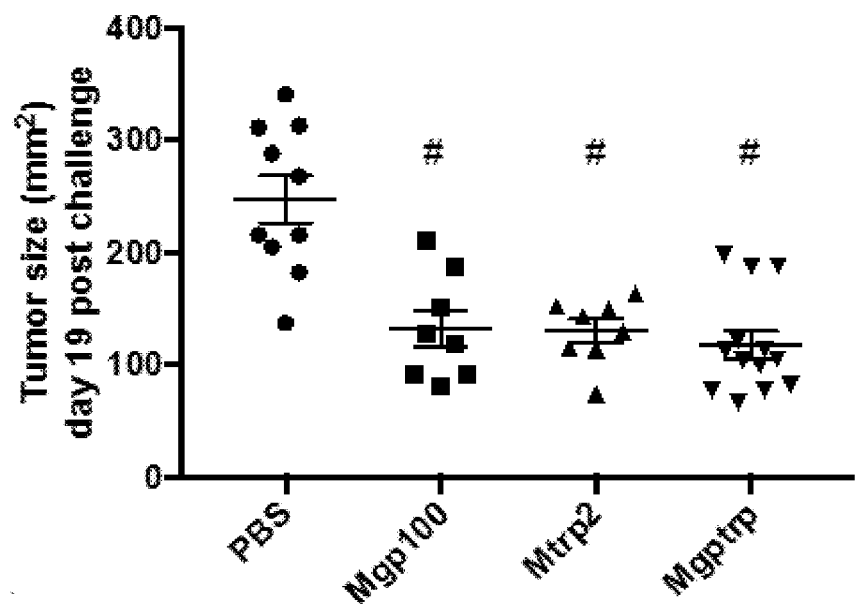
Figure 1E:
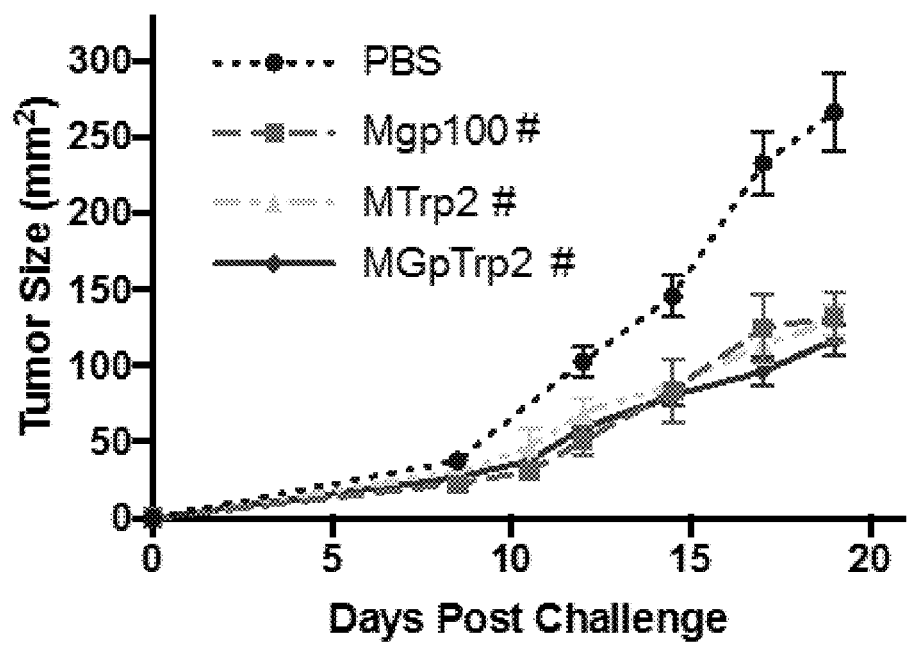
Figure 1F:
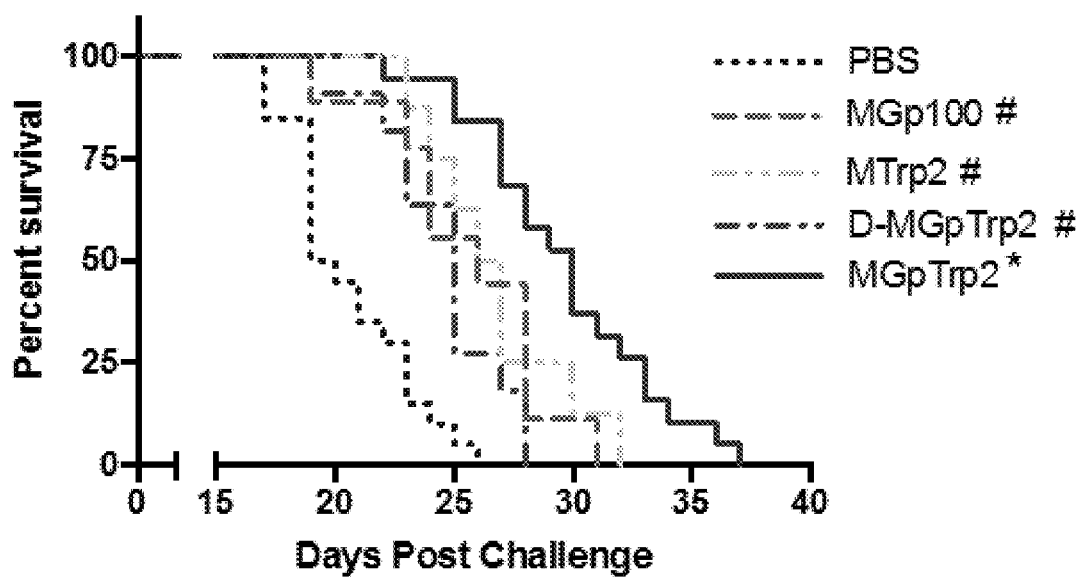

Example 1. Immunogenic Composition/Therapy Comparisons (FIG. 1A) Linear representations of expressed sequences within the immunogenic plasmid. mMIP3α is full length and functional protein. D-mMIP3α contains a C6S mutation that renders MIP3α ineffective at targeting dendritic cells. "Sp" refers to a 14 amino acid spacer sequence. "Tag" refers to a 29 amino acid region including standard myc and histidine tags. Upstream of the construct is a secretion signal sequence from the mouse IP10 gene. For FIGS. 1B-1F, MGpTrp2 refers to immunogenic nucleic acid construct encoding MIP3α, Gp100, and Trp2 antigens. Mice were challenged at day 0 with $5 \times 10^4$ B16F10 cells and vaccinated on days 5, 12, and 19 with 50 µg plasmid. (FIG. 1B) Tumor size at day 19 post challenge and (FIG. 1C) tumor growth time course from day 0 to day 21 comparing PBS control, D-MIP3α-GpTrp2, and MIP3α-GpTrp2. (FIG. 1D) Tumor size at day 19 post challenge and (FIG. 1E) tumor growth time course from day 0 to day 19 comparing PBS mock vaccination, MGp100, MTrp2, and MGpTrp2. (FIG. 1F) Kaplan-Meier survival analysis of all test groups, assessed by log-rank test. Panels B-F show data combined from two to four independent experiments, n=4-6 mice per group per experiment. Log(2) transformed tumor size data tested for significance by anova with Tukey's multiple comparison test. Tumor growth tested by Area Under the Curve calculations with non-overlapping 95% confidence intervals. Outliers more than two standard deviations from the mean were excluded from the dataset. #p<0.05 to negative control; *p<0.05 compared to all groups. Error bars denote estimate of standard error of the mean.

Figure 2A:
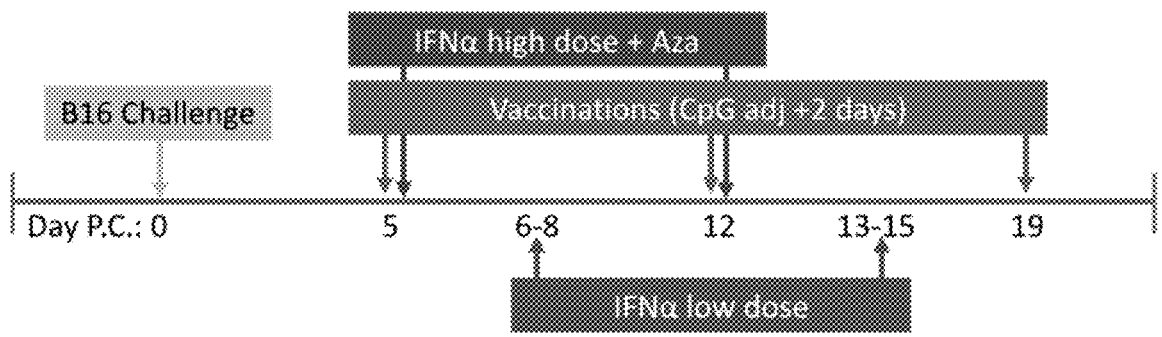
FIGS. 2A-2D: Addition of IFNα and Aza to Immunogenic Therapy.
Figure 2B:
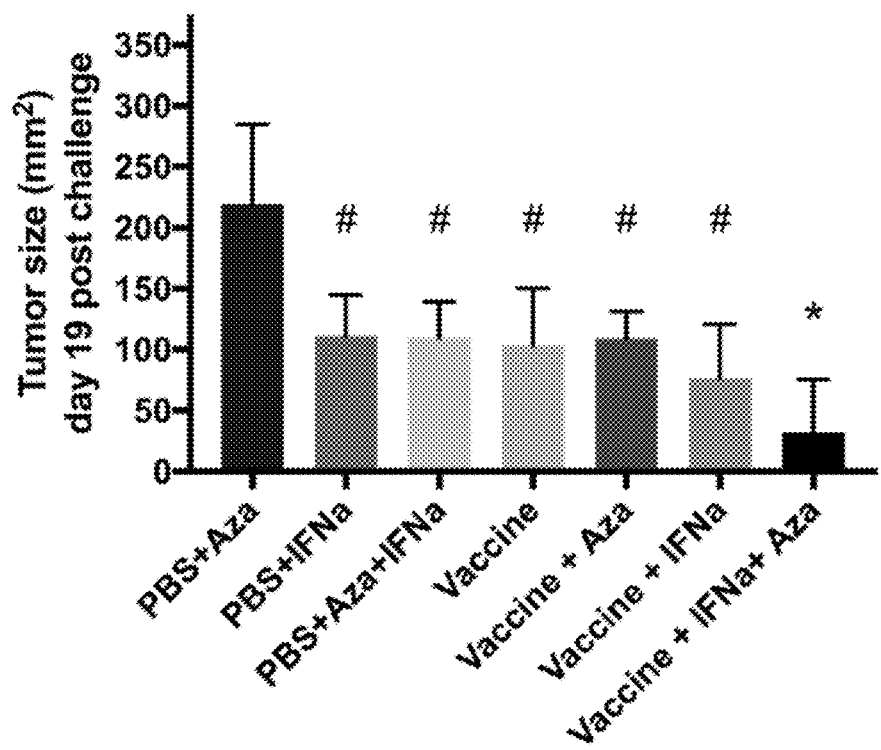
Figure 2C:
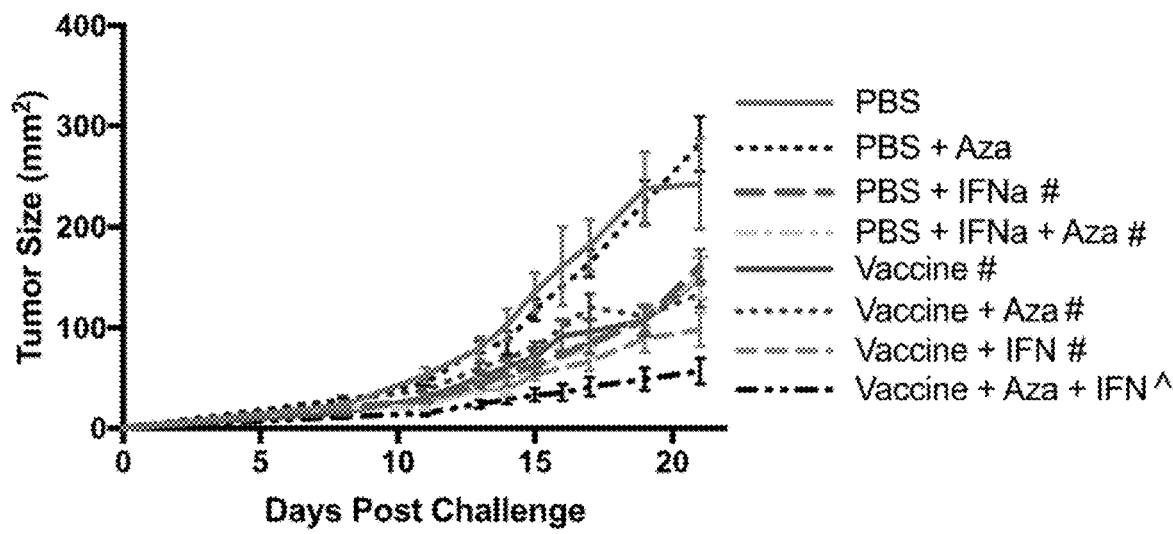
Figure 2D:
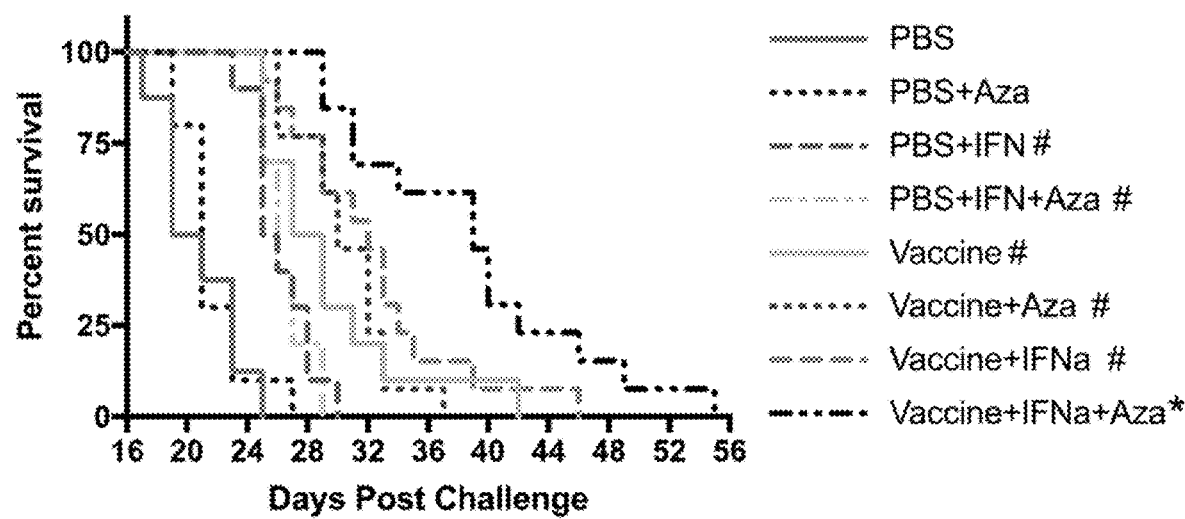

Example 2. Addition of IFNα and Aza to Therapy (FIG. 2A) Therapy schedule. At day 0 mice were challenged with $5 \times 10^4$ B6F10 cells. The immunogenic nucleic acid construct encoded MIP3α-Gp100-Trp2 and was given at 50 µg/dose followed by intramuscular (i.m.) electroporation. High dose IFNα (10,000 units) and low dose IFNα (1,000 units) were given intratumorally. Aza was given I.p. at 1 mg/kg. (FIG. 2B) Tumor sizes across groups at day 19 post challenge. PBS alone was excluded due to mice already removed from the group. Statistical analysis was performed on the log(2) transformed data values by one-way anova with Tukey's multiple comparison test. (FIG. 2C) Tumor size progression from day 0 to day 21. Significance was assessed by non-overlapping 95% confidence intervals of Area Under the Curve calculations. (FIG. 2D) Kaplan-Meier Survival curve of all groups, tested by log-rank test. (FIG. 2B-2D) Combined data from two independent experiments, n=3-8 mice per group per experiment. Outliers more than two standard deviations from the mean were excluded from the dataset. On the graphs, statistical significance ($\alpha$=0.05) is delineated by: #significant to negative control, *significant to all other groups, ˆ significant to all groups except Construct+IFN. Error bars show estimated standard error of the mean.

Surprisingly, the combination of immunogenic construct (plasmid+CpG adjuvant), IFNα, and Aza produced a synergistic response, reducing tumor size by more than 50% relative to immunogenic construct+IFNα, and relative to immunogenic construct+Aza.

Example 3. T-Cell Flow Cytometry Analysis (FIG. 3A) Therapy schedule. Vaccination and treatments are the same as outlined in FIGS. 2A-2D. This figure shows analysis of the late time point only. See FIGS. 4A-4D for analysis of the early time point. (FIGS. 3B-2C) Percentage and tumor-size normalized numbers respectively of CD3+ CD8+ tumor infiltrating lymphocytes (TILs) that were successfully stimulated by antigenic peptides. (FIGS. 3D-3E) show the percentage and tumor-size normalized numbers respectively of gated TILs that are CD3+CD4+. (FIGS. 3F-3G) show the percentage and tumor-size normalized numbers respectively of gated TILs that are CD3+CD8+. (FIGS. 3H-3I) show the scatterplots and correlations of mice from all groups comparing gated TILs that were CD3+CD4+ or CD3+CD8+ respectively to measured tumor size. All panels represent two to three independent experiments with n=3-4 mice per group per experiment. (FIGS. 3B-3G) were assessed by one-way Anova with Tukey's multiple comparison test. Significance was annotated by bars between two groups or by an asterisk where the group is significantly different from all other groups. (FIGS. 3H-3I) were tested by simple linear regression, with $R^2$ and p values noted in the panel. Error bars denote estimate for the standard error of the mean.

Example 4. Early Time Point T-Cell Analysis

Figure 3A:
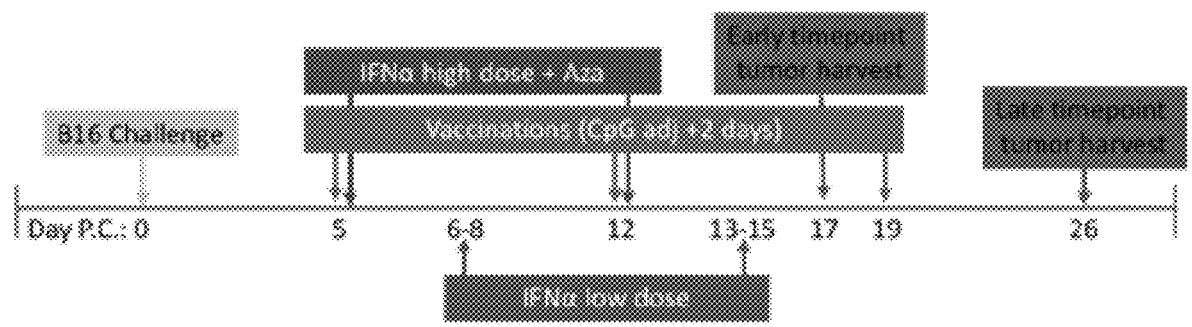
FIGS. 3A-3I: T-cell flow cytometry analysis.
Figure 3B:
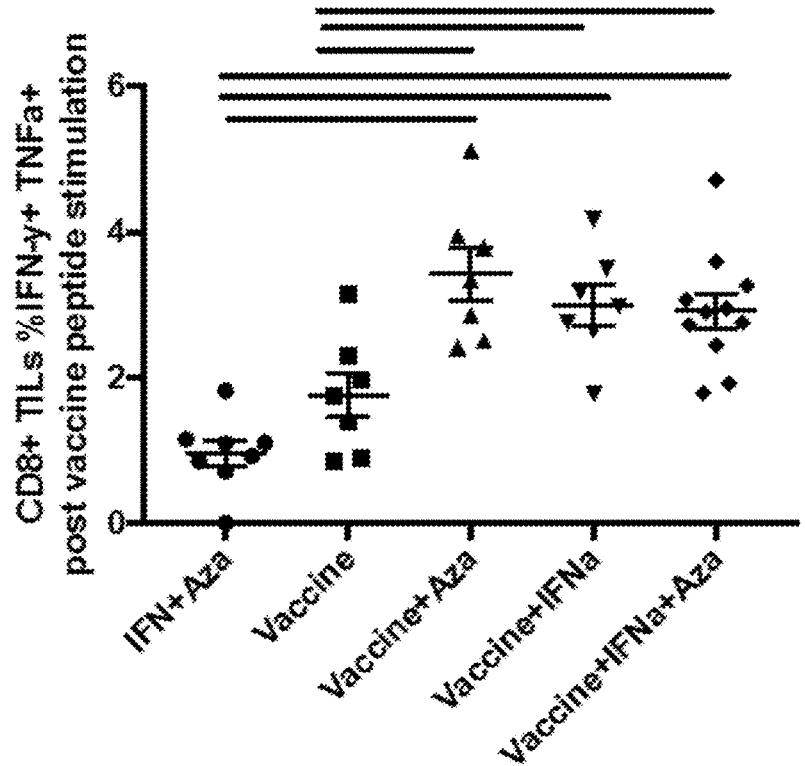
Figure 3C:
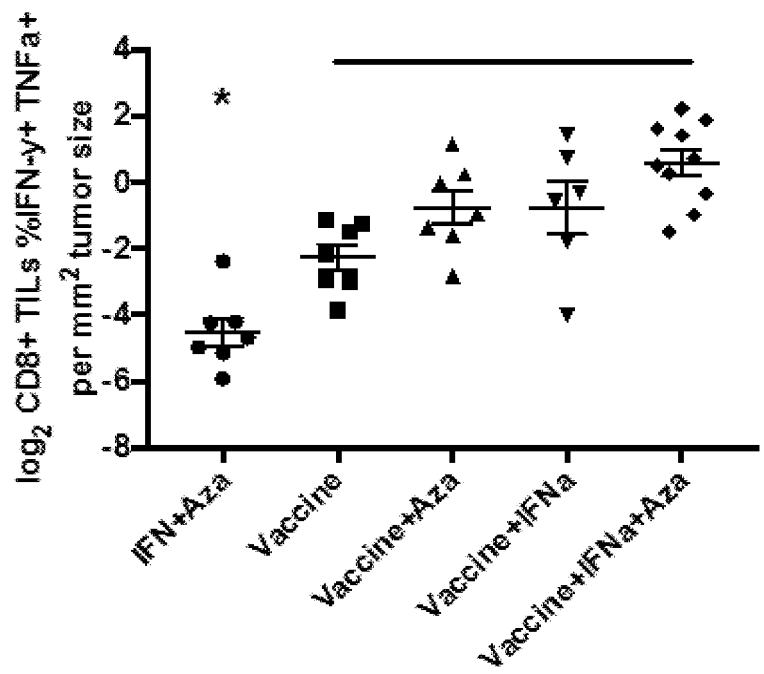
Figure 3D:
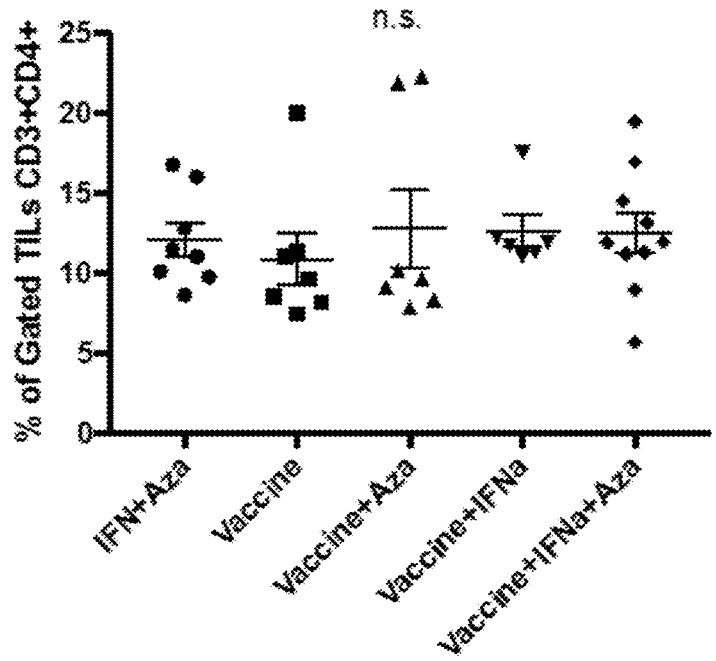
Figure 3E:
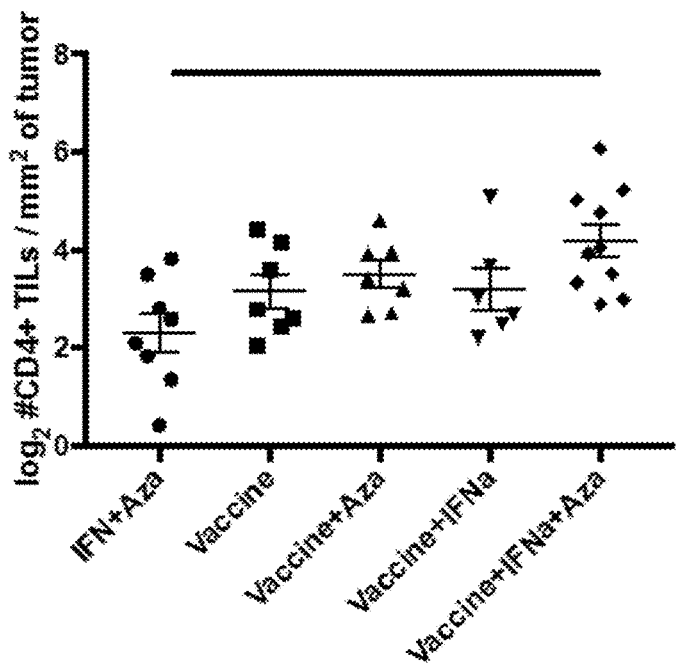
Figure 3F:
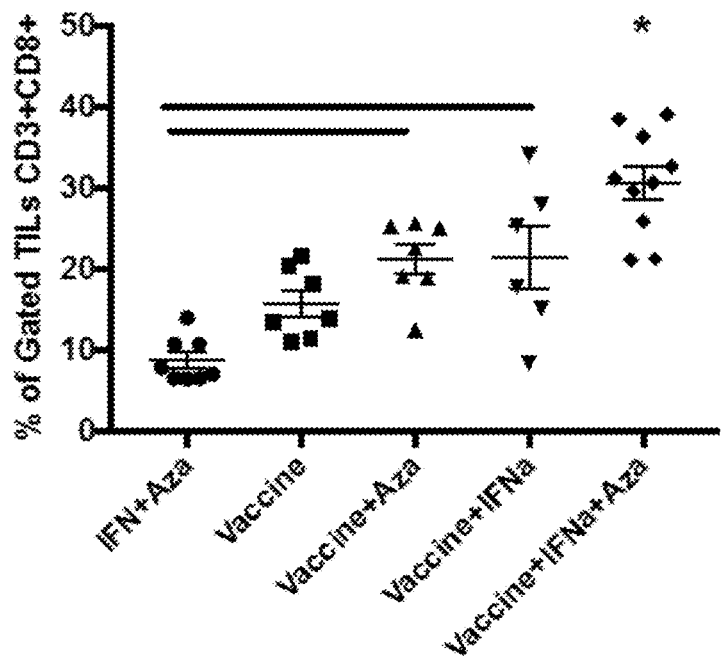
Figure 3G:
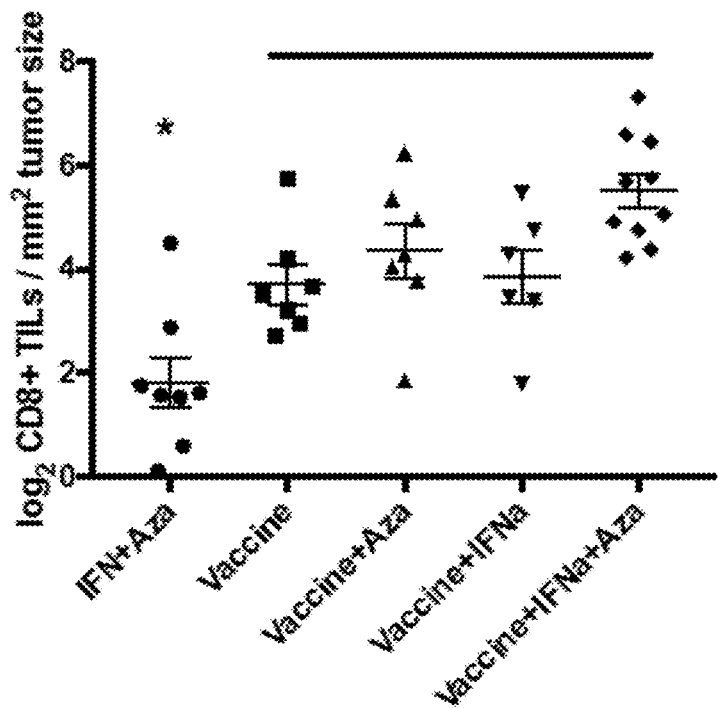
Figure 3H:
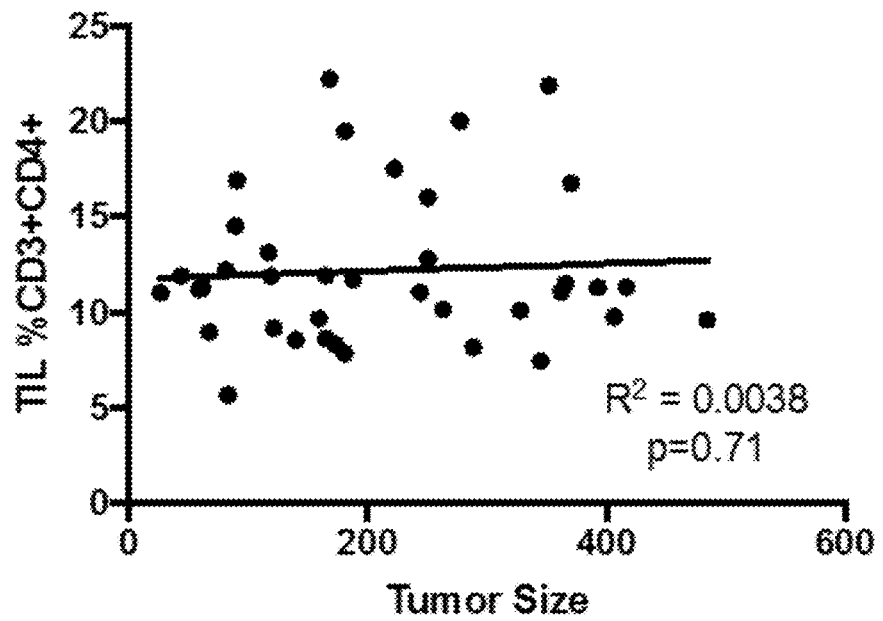
Figure 3I:
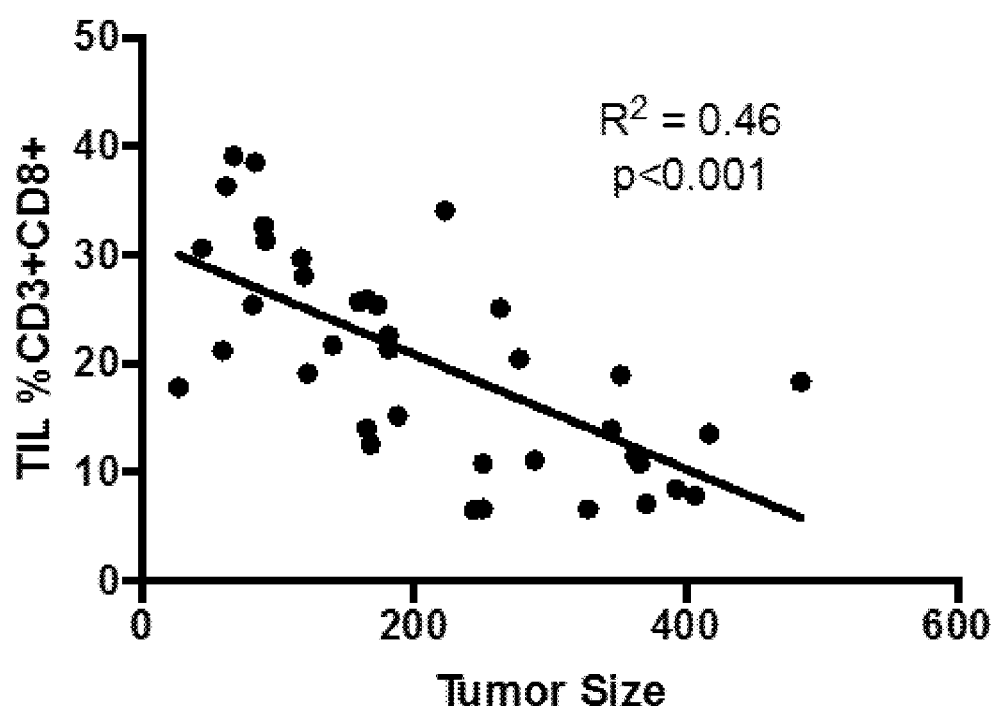
Figure 4A:
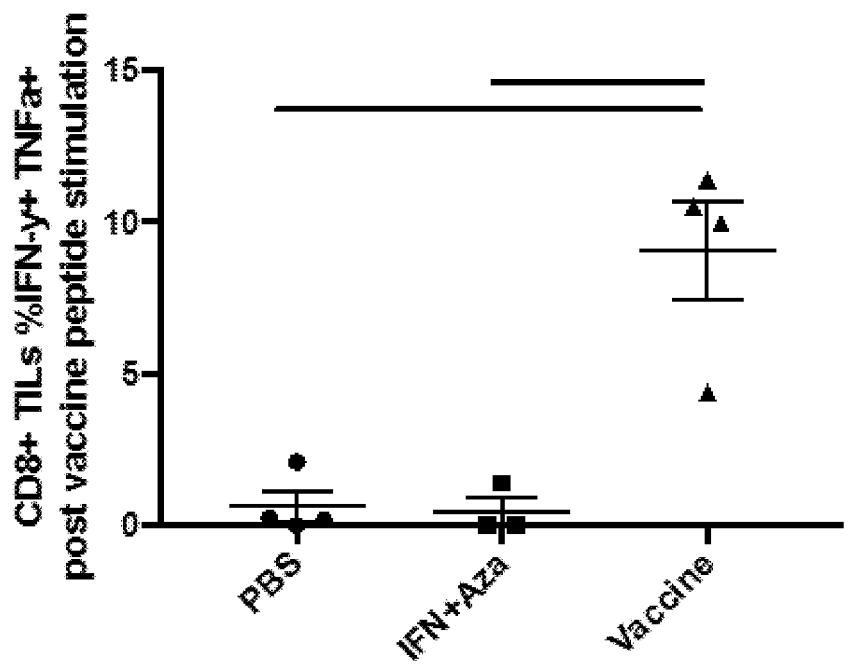
FIGS. 4A-4D: Early time point T-cell analysis. These figures follows the schedule as annotated in FIG. 3A, with tumors harvested at the designated early time point.
Figure 4B:
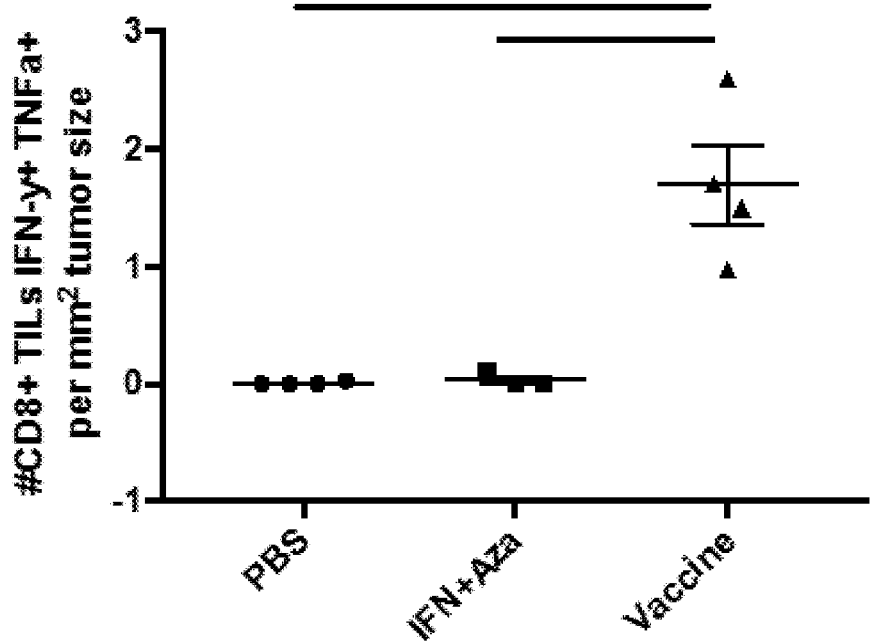
Figure 4C:
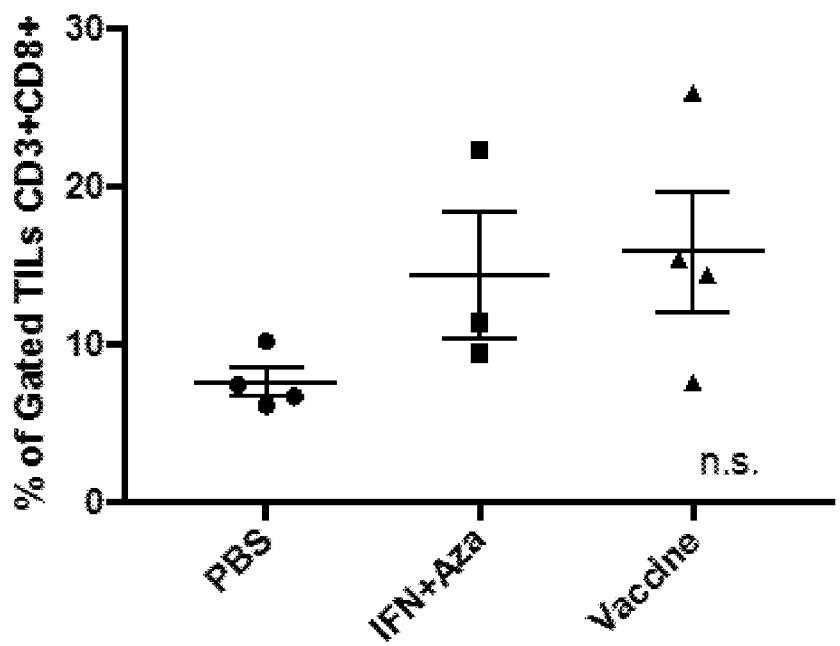
Figure 4D:
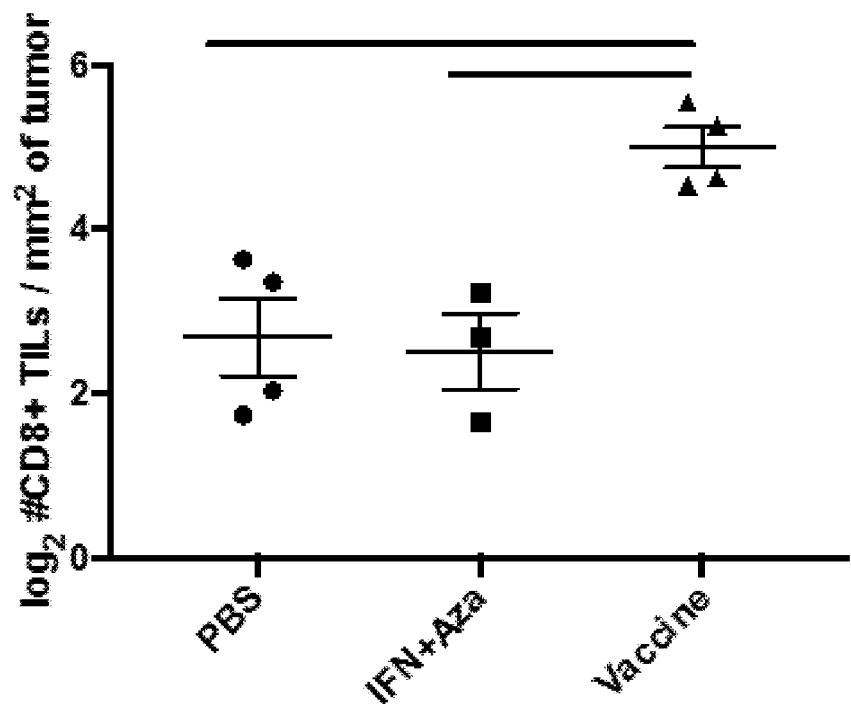

FIGS. 4A-4D follow the schedule as annotated in FIG. 3A, with tumors harvested at the designated early time point. (FIG. 4A) Percentage of and (FIG. 4B) tumor-size normalized numbers of CD3+CD8+TILs that were IFNγ and TNFα double positive after stimulation with antigenic peptides. (FIG. 4C) Percentage of and (FIG. 4D) tumor size normalized numbers of gated TILs that were CD3+CD8+. Data represented one experiment of n=3-4 mice per group. Significance tested by one-way Anova with Tukey's multiple comparisons test, with significance noted by bars between groups. Error bars are representative of estimate of the standard error of the mean.

Figure 5A:
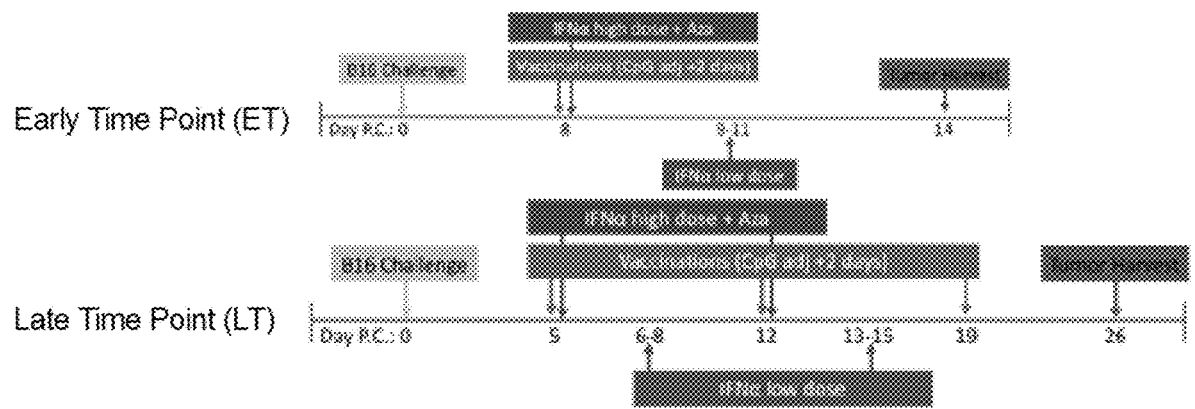
FIGS. 5A-5E: qRT-PCR analysis of gene expression.
Figure 5B:
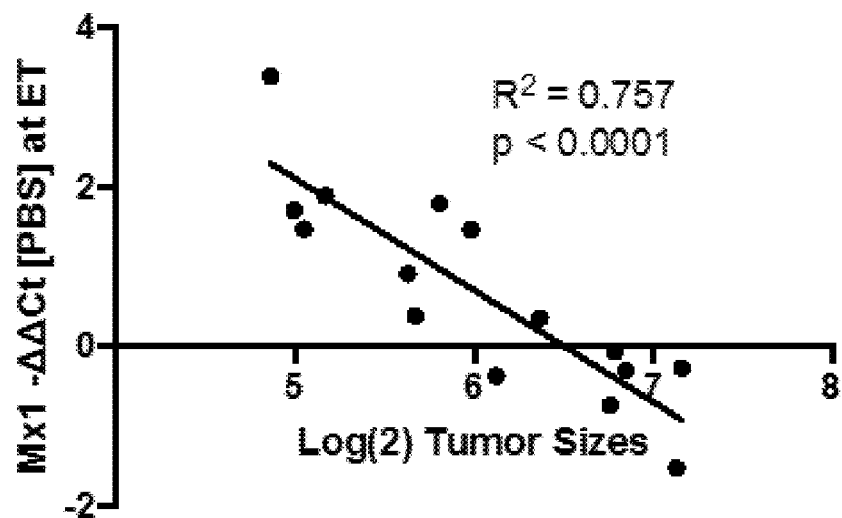
Figure 5C:
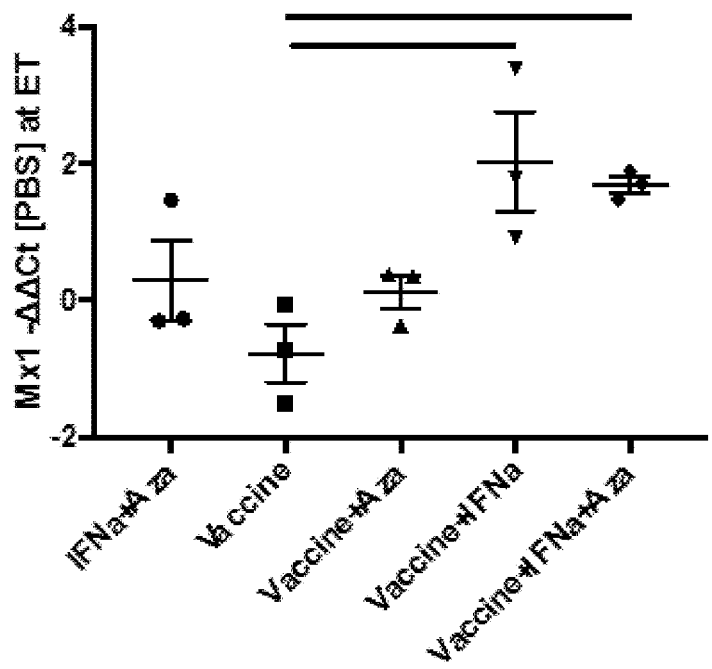
Figure 5D:
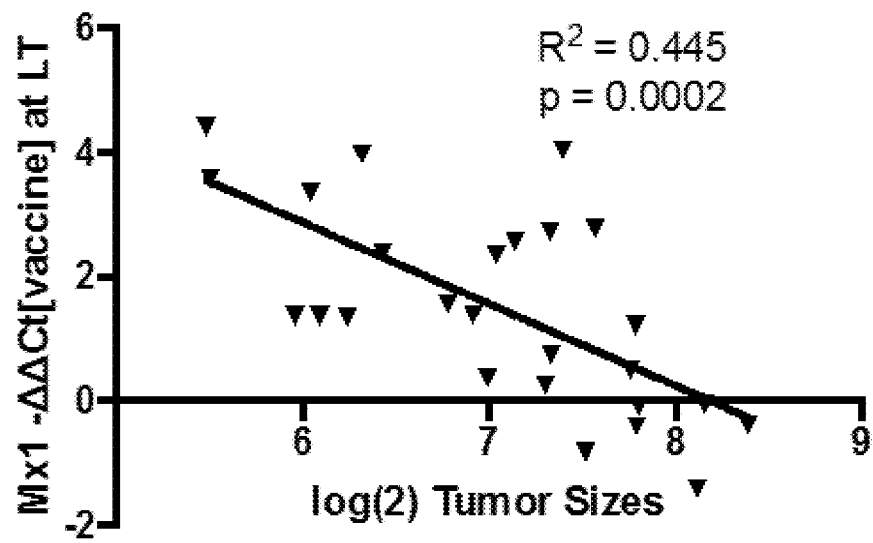
Figure 5E:
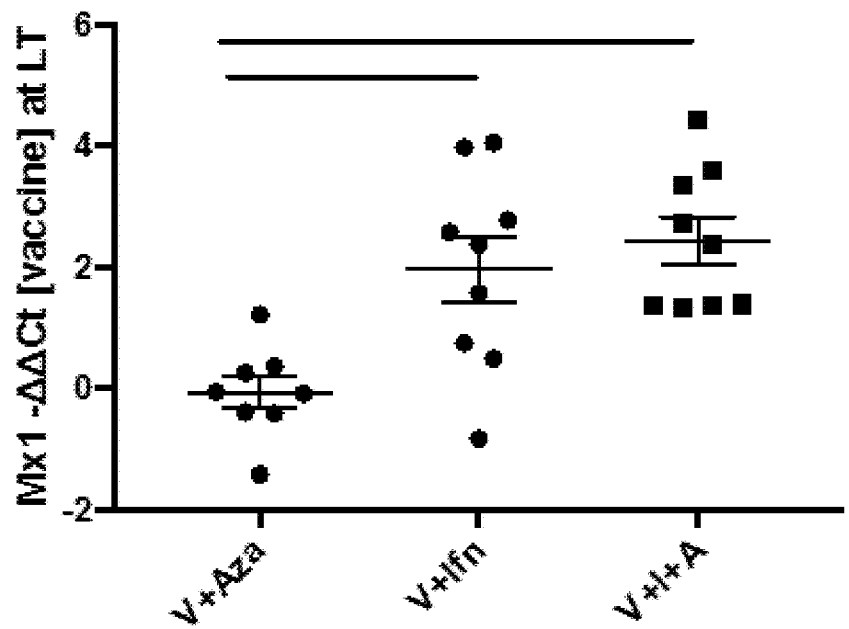

Example 5. qRT-PCR Analysis of Gene Expression (FIG. 5A) Outlines the early and late time point therapy schedules. For analysis, ΔCt is calculated by subtracting the gene of interest Ct value from housekeeping gene GAPDH for each sample. ΔΔCt is calculated by subtracting ΔCt values from gene of interest to the ΔCt value of either negative control at the early time point or vaccine-only at the late time point. (FIGS. 5B and 5D) show the overall correlation between Mx1-ΔΔCt values and tumor size at early (FIG. 5B) and late (FIG. 5D) time points. (FIGS. 5C and 5E) show the comparison across groups of Mx1-ΔΔCt values at the early and late time points respectively. The data represent two independent experiments, n=3-5 mice per group per experiment. Scatterplots were tested by simple linear regression, with $R^2$ and p values noted on the graphs. Grouped analyses were tested by Anova with Tukey's multiple comparisons test, with significant comparisons marked by bars. Error bars denote estimate of the standard error of the mean.

Example 6. Intratumoral Versus Intramuscular Administration of IFNα

Figure 6A:
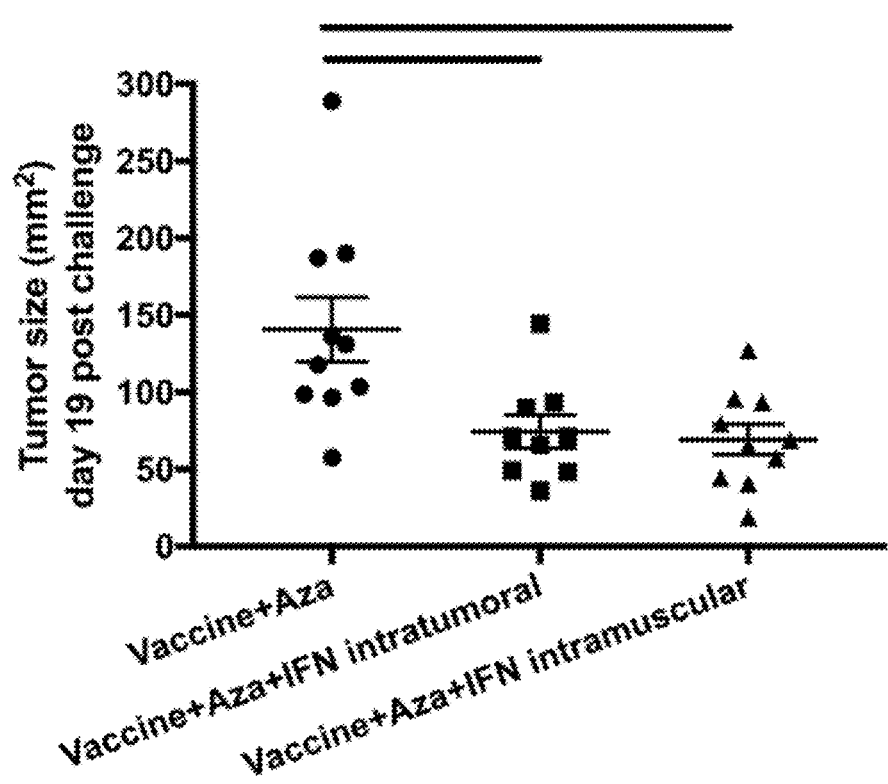
FIGS. 6A-6C: Intratumoral versus intramuscular administration of IFNα. Nucleic acid encoding MIP3α-Gp100-Trp2 was used as the immunogenic construct, with ODN2395 CpG adjuvant given two days later. Schedule of treatment is the same as FIG. 2A.
Figure 6B:
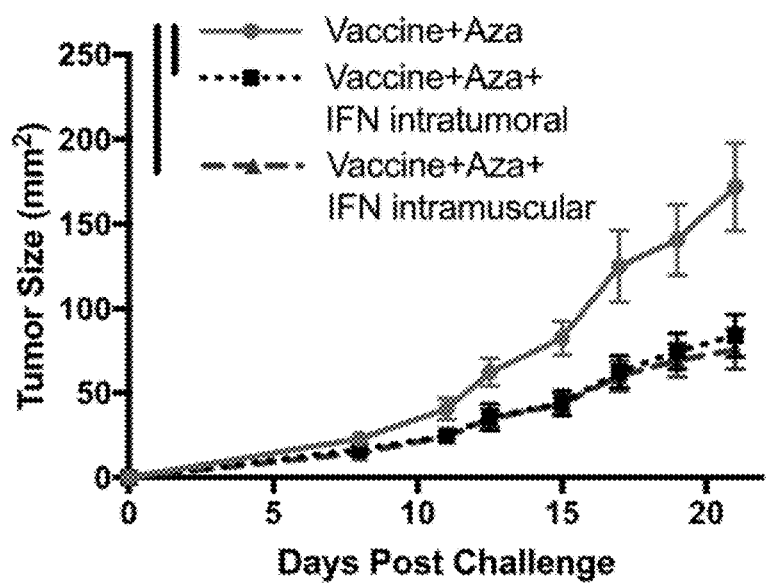
Figure 6C:
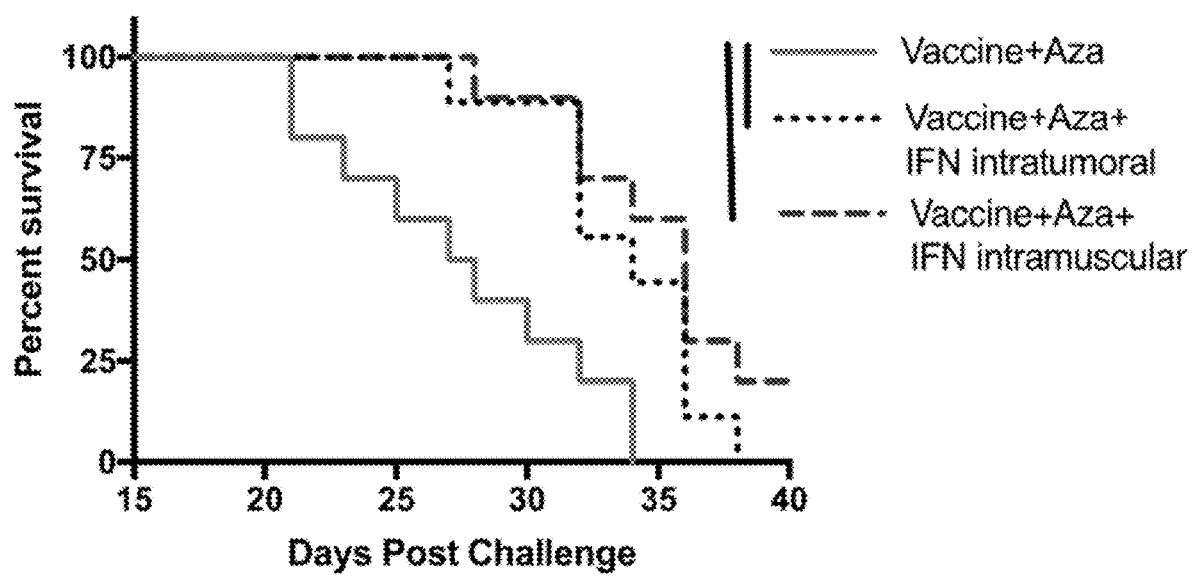

Nucleic acid encoding MIP3α-Gp100-Trp2 was used as the immunogenic composition, with ODN2395 CpG adjuvant given two days later. Schedule of treatment is the same as FIG. 2A. (FIG. 6A) Tumor Sizes at day 19 post challenge. Data were tested by one-way Anova with Tukey's multiple comparison test. (FIG. 6B) Tumor growth time course through day 21 post challenge. Area Under the Curve statistics were calculated, and interactions were considered significant if 95% confidence intervals did not overlap. (FIG. 6C) Kaplan-Meier survival curve as assessed by log-rank test. Panels A-C show combined data from two independent experiments, n=3-7 mice per group per experiment. Statistical significance designated by bars between groups, α=0.05. Error bars Error bars show estimated standard error of the mean.

Figure 7A:
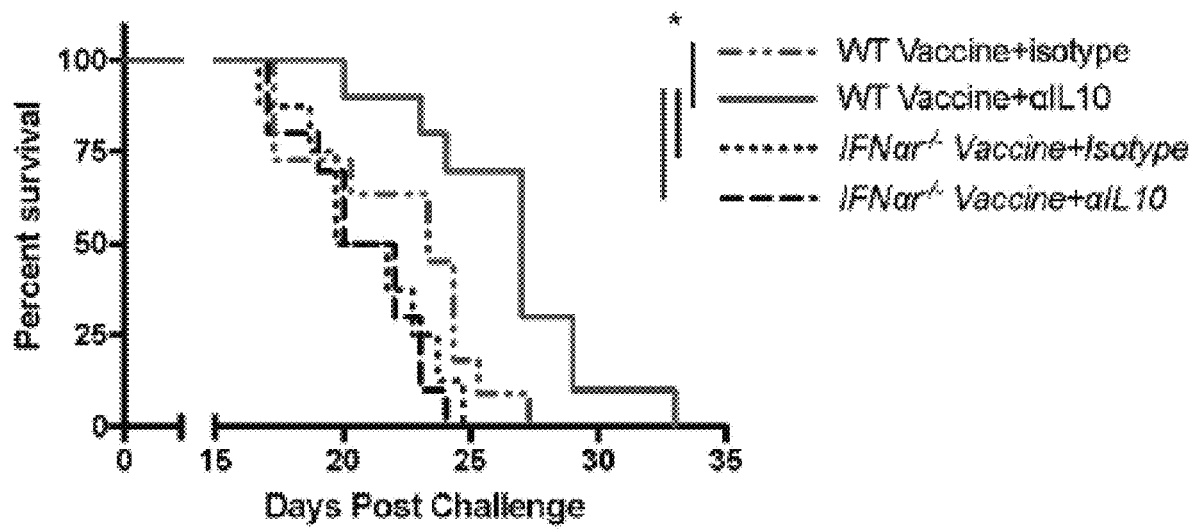
FIGS. 7A-7B: Schedule for therapy and administration of anti-IL10 and the effect of the treatments on tumor size at Day 17 post-tumor implantation and on survival. The numbers adjacent to the lines represent the corresponding slopes.
Figure 7B:
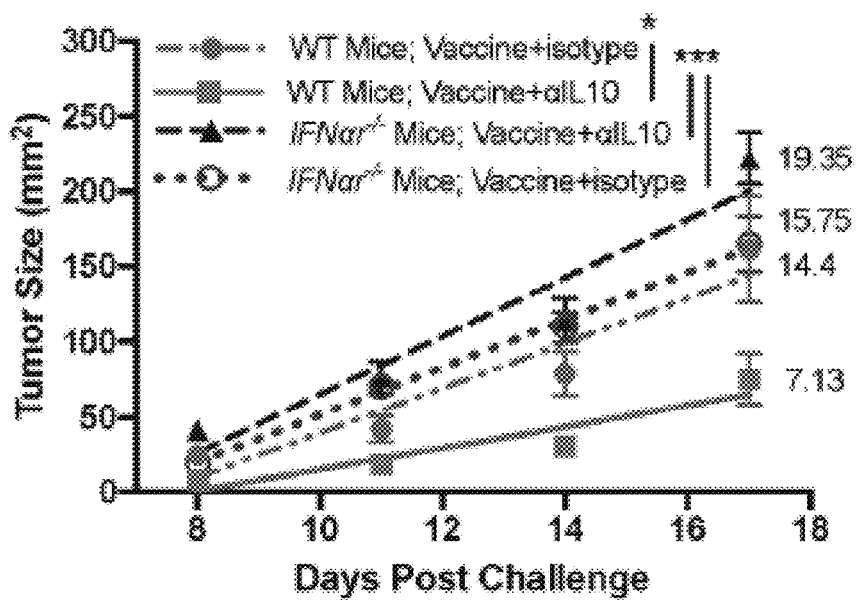
Figure 8:
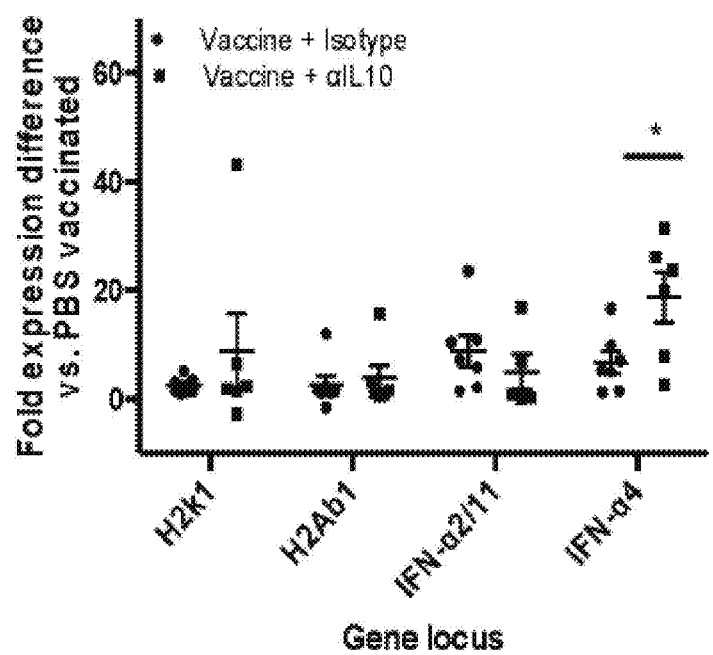
FIG. 8: Relative expression of interferon and H2 genes in mice treated or not treated with anti-IL10 in addition to immunogenic composition, as determined using the StepOnePlus™ Real time PCR system. Results were analyzed by $\Delta\Delta Ct$ Relative Quantitation Method and $\Delta Ct$ was normalized to GAPDH expression, while $\Delta\Delta Ct$ was normalized to PBS injected mice. The fold expression change was calculated by $2^{\wedge}(-\Delta\Delta Ct)$. The experiment was run twice with 3-4 mice/group in each experiment. P with vs. without anti-IL10 was <0.05.

Example 7. Schedule for Vaccination and Administration of Anti-IL10 and the Effect of the Treatments on Tumor Size at Day 17 Post-Tumor Implantation and on Survival The numbers adjacent to the lines represent the corresponding slopes. (FIG. 7A) Percent survival at indicated days post challenge. (FIG. 7B) Tumor size ($mm^2$) at indicated days post challenge.

Example 8. Relative Expression of Interferon and H2 Genes in Mice Treated or Not Treated with Anti-IL10 in Addition to Immunogenic Composition, as Determined Using the StepOnePlus™ Real Time PCR System Results were analyzed by ΔΔCt Relative Quantitation Method and ΔCt was normalized to GAPDH expression, while ΔΔCt was normalized to PBS vaccinated mice. The fold expression change was calculated by 2^(-ΔΔCt). The experiment was run twice with 3-4 mice/group in each experiment. P with vs. without anti-IL10 was <0.05.

SEQUENCES

```
>Human MIP3α
GCAGCAAGCAACTTTGACTGCTGTCTTGGATACACAGACCGTATTCTTCATCCTA
AATTTATTGTGGGCTTCACACGGCAGCTGGCCAATGAAGGCTGTGACATCAATGC
TATCATCTTTCACACAAAGAAAAAGTTGTCTGTGTGCGCAAATCCAAAACAGACT
TGGGTGAAATATATTGTGCGTCTCCTCAGTAAAAAAGTCAAGAACATG (SEQ ID NO: 7)

AASNFDCCLGYTDRILHPKFIVGFTRQLANEGCDINAIIFHTKKKLSVCANPKQTWVK
YIVRLLSKKVKNM (SEQ ID NO: 8)

>Mouse MIP3α
GCAAGCAACTACGACTG*TTGCCTCTCGTACATACAGACGCCTCTTCCTTCCAGA
GCTATTGTGGGTTTCACAAGACAGATGGCCGATGAAGCTTGTGACATTAATGCTA
TCATCTTTCACACGAAGAAAAGAAAATCTGTGTGCGCTGATCCAAAGCAGAACT
GGGTGAAAAGGGCTGTGAACCTCCTCAGCCTAAGAGTCAAGAAGATG (SEQ ID NO: 9)

ASNYDC*CLSYIQTPLPSRAIVGFTRQMADEACDINAIIFHTKKRKSVCADPKQNWVK
RAVNLLSLRVKKM (SEQ ID NO: 10)

>Human Trp2
GGCCTGCTTGGGCCCAATGGAACCCAGCCGCAGTTTGCCAACTGCAGTGTTTATG
ATTTTTTTGTGTGGCTCCATTATTATTCTGTTAGAGATACATTATTAGGACCAGGA
CGCCCCTACAGGGCCATAGATTTCTCACATCAAGGACCTGCATTTGTTACCTGGC
ACCGGTACCATTTGTTGTGTCTGGAAAGAGATCTCCAGCGACTCATTGGCAATGA
GTCTTTTGCTTTGCCCTACTGGAACTTTGCCACTGGGAGGAACGAGTGTGATGTG
TGTACAGACCAGCTGTTTGGGGCA (SEQ ID NO: 11)

GLLGPNGTQPQFANCSVYDFFVWLHYYSVRDTLLGPGRPYRAIDFSHQGPAFVTWH
RYHLLCLERDLQRLIGNESFALPYWNFATGRNECDVCTDQLFGA (SEQ ID NO: 12)
```

SEQUENCES

>Mouse Trp2
GGGCTGCTCGGACCCAACGGGACCCAGCCCCAGATCGCCAACTGCAGCGTGTAT
GACTTTTTTGTGTGGCTCCATTATTATTCTGTTCGAGACACATTATTAGGTCCAGG
ACGCCCCTATAAGGCCATTGATTTCTCTCACCAAGGGCCTGCCTTTGTCACGTGG
CACAGGTACCATCTGTTGTGGCTGGAAAGAGAACTCCAGAGACTCACTGGCAAT
GAGTCCTTTGCGTTGCCCTACTGGAACTTTGCAACCGGGAAGAACGAGTGTGACG
TGTGCACAGACGAGCTGCTTGGAGCA (SEQ ID NO: 13)

GLLGPNGTQPQIANCSVYDFFVWLHYYSVRDTLLGPGRPYKAIDFSHQGPAFVTWH
RYHLLWLERELQRLTGNESFALPYWNFATGKNECDVCTDELLGA (SEQ ID NO: 14)

>Human Gp100
AAAGTACCCAGAAACCAGGACTGGCTTGGTGTCTCAAGGCAACTCAGAACCAAA
GCCTGGAACAGGCAGCTGTATCCAGAGTGGACAGAAGCCCAGAGACTTGACTGC
TGGAGAGGTGGTCAAGTGTCCCTCAAGGTCAGTAATGATGGGCCTACACTGATTG
GTGCAAATGCCTCCTTCTCTATTGCCTTGAACTTCCCTGGAAGCCAAAAGGTATT
GCCAGATGGGCAGGTTATCTGGGTCAACAATACCATCATCAATGGGAGCCAGGT
GTGGGGAGGACAGCCAGTGTATCCCCAGGAAACTGACGATGCCTGCATCTTCCCT
GATGGTGGACCTTGCCCATCTGGCTCTTGGTCTCAGAAGAGAAGCTTTGTTTATG
TCTGGAAGACCTGGGGCCAATACTGGCAAGTTCTAGGGGCCCAGTGTCTGGGC
TGAGCATTGGGACAGGCAGGGCAATGCTGGGCACACACACCATGGAAGTGACTG
TCTACCATCGCCGGGGATCCCGGAGCTATGTGCCTCTTGCTCATTCCAGCTCAGC
CTTCACCATTACTGACCAGGTGCCTTTCTCCGTGAGCGTGTCCCAGTTGCGGGCCT
TGGATGGAGGGAACAAGCACTTCCTGAGAAAT (SEQ ID NO: 15)

KVPRNQDWLGVSRQLRTKAWNRQLYPEWTEAQRLDCWRGGQVSLKVSNDGPTLIG
ANASFSIALNFPGSQKVLPDGQVIWVNNTIINGSQVWGGQPVYPQETDDACIFPDGG
PCPSGSWSQKRSFVYVWKTWGQYWQVLGGPVSGLSIGTGRAMLGTHTMEVTVYH
RRGSRSYVPLAHSSSAFTITDQVPFSVSVSQLRALDGGNKHFLRN (SEQ ID NO: 16)

(mouse)MIP3α-(human)Gp100-(mouse)Trp2 construct in pCMVEa/b
mammalian protein expression plasmid
<CTGCAG>AACACC(ATG)/AACCCAAGTGCTGCCGTCATTTTCTGCCTCATCCTGC
TGGGTCTGAGTGGGACTCAAGGGATC/CTCGACATGGCAAGCAACTACGACTG*T
TGCCTCTCGTACATACAGACGCCTCTTCCTTCCAGAGCTATTGTGGGTTTCACAAG
ACAGATGGCCGATGAAGCTTGTGACATTAATGCTATCATCTTTCACACGAAGAAA
AGAAAATCTGTGTGCGCTGATCCAAAGCAGAACTGGGTGAAAAGGGCTGTGAAC
CTCCTCAGCCTAAGAGTCAAGAAGATGGAATTCAACGACGCTCAGGCGCCGAAGAG
TCTCGAGGCTAGAAAAGTACCCAGAAACCAGGACTGGCTTGGTGTCTCAAGGC
AACTCAGAACCAAAGCCTGGAACAGGCAGCTGTATCCAGAGTGGACAGAAGAAG
CCCAGAGACTTGACTGCTGGAGAGGTGGTCAAGTGTCCCTCAAGGTCAGTA
ATGATGGGCCTACACTGATTGGTGCAAATGCCTCCTTCTCTATTGCCTTGAA
CTTCCCTGGAAGCCAAAAGGTATTGCCAGATGGGCAGGTTATCTGGGTCAA
CAATACCATCATCAATGGGAGCCAGGTGTGGGGAGGACAGCCAGTGTATCC
CCAGGAAACTGACGATGCCTGCATCTTCCCTGATGGTGGACCTTGCCCATCT
GGCTCTTGGTCTCAGAAGAGAAGCTTTGTTTATGTCTGGAAGACCTGGGGC
CAATACTGGCAAGTTCTAGGGGCCCAGTGTCTGGGCTGAGCATTGGGACA
GGCAGGGCAATGCTGGGCACACACACCATGGAAGTGACTGTCTACCATCGC
CGGGGATCCCGGAGCTATGTGCCTCTTGCTCATTCCAGCTCAGCCTTCACCA
TTACTGACCAGGTGCCTTTCTCCGTGAGCGTGTCCCAGTTGCGGGCCTTGG
ATGGAGGGAACAAGCACTTCCTGAGAAA<TCTAGA>AATGGAGTTCAACGACGC
TCAGGCGCCGAAGAGTCTCGAAGCTGGGCTGCTCGGACCCAACGGGACCCAGCCC
CAGATCGCCAACTGCAGCGTGTATGACTTTTTTGTGTGGCTCCATTATTATTCTGT
TCGAGACACATTATTAGGTCCAGGACGCCCCTATAAGGCCATTGATTTCTCTCAC
CAAGGGCCTGCCTTTGTCACGTGGCACAGGTACCATCTGTTGTGGCTGGAAAGAG
AACTCCAGAGACTCACTGGCAATGAGTCCTTTGCGTTGCCCTACTGGAACTTTGC
AACCGGGAAGAACGAGTGTGACGTGTGCACAGACGAGCTGCTTGGAGCAGCGCG
GCCGCAGTCGAC<TCTAGA>GAGATCCGCAGAA{GAACAGAAACTGATCTCAGA
AGAGGATCTG}GCC[CACCACCATCACCATCAC](TAA)<CCCGGG> (SEQ ID NO: 17)

(M)/NPSAAVIFCLILLGLSGTQGI/LDMASNYDC*CLSYIQTPLPSRAIVGFTRQMADEA
CDINAIIFHTKKRKSVCADPKQNWVKRAVNLLSLRVKKMEFNDAQAPKSLEARKVPR
NQDWLGVSRQLRTKAWNRQLYPEWTEAQRLDCWRGGQVSLKVSNDGPTLIG
ANASFSIALNFPGSQKVLPDGQVIWYNNTIINGSQVWGGQPVYPQETDDACIFPD
GGPCPSGSWSQKRSFVYVWKTWGQYWQVLGGPVSGLSIGTGRAMLGTHTME
VTVYHRRGSRSYVPLAHSSSAFTITDQVPFSVSVSQLRALDGGNKHFLR<NLE>M
EFNDAQAPKSLEAGLLGPNGTQPQIANCSVYDFFVWLHYYSVRDTLLGPGRPYKAIDF
SHQGPAFVTWHRYHLLWLERELQRLTGNESFALPYWNFATGKNECDVCTDELLGA
ARPQS<TLE>RSAE{EQKLISEEDL}A[HHHHHH](.) (SEQ ID NO: 18)

(human)MIP3α-(human)Gp100-(human)Trp2 construct in pCMVEa/b
mammalian protein expression plasmid
<CTGCAG>AACACC(ATG)/GATGCAATGAAGAGAGGGCTCTGCTGTGTGCTGCTG
CTGTGTGGAGCAGTCTTCGTTTCGCCCAGC/CTCGACATGGCAGCAAGCAACTTTG
ACTG*CTGTCTTGGATACACAGACCGTATTCTTCATCCTAAATTTATTGTGGGCTT
CACACGGCAGCTGGCCAATGAAGGCTGTGACATCAATGCTATCATCTTTCACACA

SEQUENCES

```
AAGAAAAAGTTGTCTGTGTGCGCAAATCCAAAACAGACTTGGGTGAAATATATT
GTGCGTCTCCTCAGTAAAAAAGTCAAGAACATGGAATTCAACGACGCTCAGGCGC
CGAAGAGTCTCGAGGCTAGAAAAGTACCCAGAAACCAGGACTGGCTTGGTGTC
TCAAGGCAACTCAGAACCAAAGCCTGGAACAGGCAGCTGTATCCAGAGTGG
ACAGAAGCCCAGAGACTTGACTGCTGGAGAGGTGGTCAAGTGTCCCTCAAG
GTCAGTAATGATGGGCCTACACTGATTGGTGCAAATGCCTCCTTCTCTATTG
CCTTGAACTTCCCTGGAAGCCAAAAGGTATTGCCAGATGGGCAGGTTATCT
GGGTCAACAATACCATCATCAATGGGAGCCAGGTGTGGGGAGGACAGCCAG
TGTATCCCCAGGAAACTGACGATGCCTGCATCTTCCCTGATGGTGGACCTTG
CCCATCTGGCTCTTGGTCTCAGAAGAGAAGCTTTGTTTATGTCTGGAAGACC
TGGGGCCAATACTGGCAAGTTCTAGGGGGCCCAGTGTCTGGGCTGAGCATT
GGGACAGGCAGGGCAATGCTGGGCACACACACCATGGAAGTGACTGTCTAC
CATCGCCGGGGATCCCGGAGCTATGTGCCTCTTGCTCATTCCAGCTCAGCCT
TCACCATTACTGACCAGGTGCCTTTCTCCGTGAGCGTGTCCCAGTTGCGGGC
CTTGGATGGAGGGAACAAGCACTTCCTGAGAAA<TCTAGA>AATGGAGTTCAAC
GACGCTCAGGCGCCGAAGAGTCTCGAAGCTGGCCTGCTTGGGCCCAATGGAACCCA
GCCGCAGTTTGCCAACTGCAGTGTTTATGATTTTTTTGTGTGGCTCCATTATTATT
CTGTTAGAGATACATTATTAGGACCAGGACGCCCCTACAGGGCCATAGATTTCTC
ACATCAAGGACCTGCATTTGTTACCTGGCACCGGTACCATTTGTTGTGTCTGGAA
AGAGATCTCCAGCGACTCATTGGCAATGAGTCTTTTGCTTTGCCCTACTGGAACT
TTGCCACTGGGAGGAACGAGTGTGATGTGTGTACAGACCAGCTGTTTGGGGCAG
CGCGGCCGCAGTCGAC<TCTAGA>GAGATCCGCAGAA{GAACAGAAACTGATCTC
AGAAGAGGATCTG}GCC[CACCACCATCACCATCAC](TAA)<CCCGGG> (SEQ ID NO: 19)

(M)/DAMKRGLCCVLLLCGAVFVSPS/LDMAASNFDC*CLGYTDRILHPKFIVGFTRQL
ANEGCDINAIIPHTKKKLSVCANPKQTWVKYIVRLLSKKVKNMEFNDAQAPKSLEAR
KVPRNQDWLGVSRQLRTKAWNRCILYPEWTEAQRLDCWRGGQVSLKVSNDGP
TLIGANASFSIALNFPGSQKVLPDGQVIWYNNTIINGSQVWGGQPVYPQETDDAC
IFPDGGPCPSGSWSQKRSFVYVWKTWGQYWQVLGGPVSGLSIGTGRAMLGTH
TMEVTVYHRRGSRSYVPLAHSSSAFTITDQVPFSVSVSOLRALDGGNKHFLR<NL
E>MEFNDAQAPKSLEAGLLGPNGTQPQFANCSVYDFFVWLHYYSVRDTLLGPGRPYR
AIDFSHQGPAFVTWHRYHLLCLERDLQRLIGNESFALPYWNFATGRNECDVCTDQLF
GAARPQS<TLE>RSAE{EQKLISEEDL}A[HHHHHH](.) (SEQ ID NO: 20)
```

Key constructs above:
(Parentheses): Start and Stop codons
[Brackets]: Histidine Tag. This tag is used for in vitro purification and/or identification.
<Wedges>: Restriction sites utilized. For initial Gp100 only plasmid: 5' end PstI; 3' XmaI/SmaI Then, Trp2 sequence inserted by XbaI on both 5' and 3' ends.
Underlined: MIP3α sequence
*Asterisked: Mutated in control plasmid with defective MIP3α. Guanine changed to cytosine, changing the cysteine amino acid to serine (C6S). This abrogates the function of MIP3α without changing the length of the construct.
Italics: Spacer sequence to allow MIP3α and gp100 to fold correctly. Similar spacer between Gp100 and Trp2 sequences
Bold: Gp100, amino acids 25-235
Double underline: Trp2 (mouse) amino acids 170-269; Trp2 (human) amino acids 165-264 of NCBI NP_001913.2
{Braces}: c-myc tag. This is a standard in vitro tag that allows for easy and specific detection of protein in western blots, elisas, and other antibody-based assays.
/Slashes/: Mouse IP-10 Leader sequence. IP-10 is a secreted mouse cytokine.

Example Signal Peptides

Gaussia luciferase
(SEQ ID NO: 21)
MGVKVLFALICIAVAEA

Human albumin
(SEQ ID NO: 22)
MKWVTFISLLFLFSSAYS

Human chymotrypsinogen
(SEQ ID NO: 23)
MAFLWLLSCWALLGTTFG

Human interleukin-2
(SEQ ID NO: 24)
MQLLSCIALILALV

Human trypsinogen-2
(SEQ ID NO: 25)
MNLLLILTFVAAAVA

Tissue plasminogen activator
(SEQ ID NO: 26)
MDAMKRGLCCVLLLCGAVFVSPS

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

What is claimed is:

1. An engineered nucleic acid comprising the sequence of SEQ ID NO: 19 or encoding the sequence of SEQ ID NO: 20.

\* \* \* \* \*

```
                         SEQUENCE LISTING

<160> NUMBER OF SEQ ID NOS: 26

<210> SEQ ID NO 1
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 1

Met Glu Phe Asn Asp Ala Gln Ala Pro Lys Ser Leu Glu Ala
1               5                   10

<210> SEQ ID NO 2
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 2
ctcgagagtc tcgaagctgg gctggt                                            26

<210> SEQ ID NO 3
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 3
ctgttcttct gcggatctct ctagagtcg                                         29

<210> SEQ ID NO 4
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 4

Lys Val Pro Arg Asn Gln Asp Trp Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 5

Ser Val Tyr Asp Phe Phe Val Trp Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic polypeptide
```

<400> SEQUENCE: 6

Tyr Pro Tyr Asp Val Pro Asp Tyr Ala
1               5

<210> SEQ ID NO 7
<211> LENGTH: 213
<212> TYPE: DNA
<213> ORGANISM: Homo sapiens

<400> SEQUENCE: 7
gcagcaagca actttgactg ctgtcttgga tacacagacc gtattcttca tcctaaattt    60
attgtgggct tcacacggca gctggccaat gaaggctgtg acatcaatgc tatcatcttt   120
cacacaaaga aaaagttgtc tgtgtgcgca atccaaaac agacttgggt gaaatatatt    180
gtgcgtctcc tcagtaaaaa agtcaagaac atg                                213

<210> SEQ ID NO 8
<211> LENGTH: 71
<212> TYPE: PRT
<213> ORGANISM: Homo sapiens

<400> SEQUENCE: 8

Ala Ala Ser Asn Phe Asp Cys Cys Leu Gly Tyr Thr Asp Arg Ile Leu
1               5                   10                  15

His Pro Lys Phe Ile Val Gly Phe Thr Arg Gln Leu Ala Asn Glu Gly
                20                  25                  30

Cys Asp Ile Asn Ala Ile Ile Phe His Thr Lys Lys Leu Ser Val
            35                  40                  45

Cys Ala Asn Pro Lys Gln Thr Trp Val Lys Tyr Ile Val Arg Leu Leu
    50                  55                  60

Ser Lys Lys Val Lys Asn Met
65                  70

<210> SEQ ID NO 9
<211> LENGTH: 210
<212> TYPE: DNA
<213> ORGANISM: Mus musculus
<220> FEATURE:
<221> NAME/KEY: misc_feature
<222> LOCATION: (17)..(17)
<223> OTHER INFORMATION: may be cytosine

<400> SEQUENCE: 9
gcaagcaact acgactgttg cctctcgtac atacagacgc ctcttccttc cagagctatt    60
gtgggtttca caagacagat ggccgatgaa gcttgtgaca ttaatgctat catctttcac   120
acgaagaaaa gaaatctgt gtgcgctgat ccaaagcaga actgggtgaa aagggctgtg    180
aacctcctca gcctaagagt caagaagatg                                    210

<210> SEQ ID NO 10
<211> LENGTH: 70
<212> TYPE: PRT
<213> ORGANISM: Mus musculus
<220> FEATURE:
<221> NAME/KEY: MISC_FEATURE
<222> LOCATION: (6)..(6)
<223> OTHER INFORMATION: may be serine

<400> SEQUENCE: 10

Ala Ser Asn Tyr Asp Cys Cys Leu Ser Tyr Ile Gln Thr Pro Leu Pro
1               5                   10                  15

| Ser | Arg | Ala | Ile | Val | Gly | Phe | Thr | Arg | Gln | Met | Ala | Asp | Glu | Ala | Cys |
| | | | 20 | | | | 25 | | | | 30 | | | | |

| Asp | Ile | Asn | Ala | Ile | Ile | Phe | His | Thr | Lys | Lys | Arg | Lys | Ser | Val | Cys |
| | | | 35 | | | | 40 | | | | 45 | | | | |

| Ala | Asp | Pro | Lys | Gln | Asn | Trp | Val | Lys | Arg | Ala | Val | Asn | Leu | Leu | Ser |
| 50 | | | | | 55 | | | | 60 | | | | | | |

| Leu | Arg | Val | Lys | Lys | Met |
| 65 | | | | 70 | |

<210> SEQ ID NO 11
<211> LENGTH: 300
<212> TYPE: DNA
<213> ORGANISM: Homo sapiens

<400> SEQUENCE: 11

```
ggcctgcttg ggcccaatgg aacccagccg cagtttgcca actgcagtgt ttatgatttt      60
tttgtgtggc tccattatta ttctgttaga gatacattat taggaccagg acgcccctac     120
agggccatag atttctcaca tcaaggacct gcatttgtta cctggcaccg gtaccatttg     180
ttgtgtctgg aaagagatct ccagcgactc attggcaatg agtcttttgc tttgccctac     240
tggaactttg ccactgggag gaacgagtgt gatgtgtgta cagaccagct gtttggggca     300
```

<210> SEQ ID NO 12
<211> LENGTH: 100
<212> TYPE: PRT
<213> ORGANISM: Homo sapiens

<400> SEQUENCE: 12

| Gly | Leu | Leu | Gly | Pro | Asn | Gly | Thr | Gln | Pro | Gln | Phe | Ala | Asn | Cys | Ser |
| 1 | | | | 5 | | | | | 10 | | | | | 15 | |

| Val | Tyr | Asp | Phe | Phe | Val | Trp | Leu | His | Tyr | Tyr | Ser | Val | Arg | Asp | Thr |
| | | | 20 | | | | 25 | | | | 30 | | | | |

| Leu | Leu | Gly | Pro | Gly | Arg | Pro | Tyr | Arg | Ala | Ile | Asp | Phe | Ser | His | Gln |
| | | | 35 | | | | 40 | | | | 45 | | | | |

| Gly | Pro | Ala | Phe | Val | Thr | Trp | His | Arg | Tyr | His | Leu | Leu | Cys | Leu | Glu |
| | 50 | | | | 55 | | | | 60 | | | | | | |

| Arg | Asp | Leu | Gln | Arg | Leu | Ile | Gly | Asn | Glu | Ser | Phe | Ala | Leu | Pro | Tyr |
| 65 | | | | 70 | | | | | 75 | | | | | 80 | |

| Trp | Asn | Phe | Ala | Thr | Gly | Arg | Asn | Glu | Cys | Asp | Val | Cys | Thr | Asp | Gln |
| | | | 85 | | | | 90 | | | | 95 | | | | |

| Leu | Phe | Gly | Ala |
| | | | 100 |

<210> SEQ ID NO 13
<211> LENGTH: 300
<212> TYPE: DNA
<213> ORGANISM: Mus musculus

<400> SEQUENCE: 13

```
gggctgctcg gacccaacgg gacccagccc cagatcgcca actgcagcgt gtatgacttt      60
tttgtgtggc tccattatta ttctgttcga gacacattat taggtccagg acgcccctat     120
aaggccattg atttctctca ccaagggcct gcctttgtca cgtggcacag gtaccatctg     180
ttgtggctgg aaagagaact ccagagactc actggcaatg agtcctttgc gttgccctac     240
tggaactttg caaccgggaa gaacgagtgt gacgtgtgca cagacgagct gcttggagca     300
```

<210> SEQ ID NO 14
<211> LENGTH: 100
<212> TYPE: PRT
<213> ORGANISM: Mus musculus

<400> SEQUENCE: 14

Gly Leu Leu Gly Pro Asn Gly Thr Gln Pro Gln Ile Ala Asn Cys Ser
1               5                   10                  15

Val Tyr Asp Phe Phe Val Trp Leu His Tyr Tyr Ser Val Arg Asp Thr
            20                  25                  30

Leu Leu Gly Pro Gly Arg Pro Tyr Lys Ala Ile Asp Phe Ser His Gln
        35                  40                  45

Gly Pro Ala Phe Val Thr Trp His Arg Tyr His Leu Leu Trp Leu Glu
    50                  55                  60

Arg Glu Leu Gln Arg Leu Thr Gly Asn Glu Ser Phe Ala Leu Pro Tyr
65                  70                  75                  80

Trp Asn Phe Ala Thr Gly Lys Asn Glu Cys Asp Val Cys Thr Asp Glu
                85                  90                  95

Leu Leu Gly Ala
            100

<210> SEQ ID NO 15
<211> LENGTH: 633
<212> TYPE: DNA
<213> ORGANISM: Homo sapiens

<400> SEQUENCE: 15
aaagtaccca gaaaccagga ctggcttggt gtctcaaggc aactcagaac caaagcctgg      60
aacaggcagc tgtatccaga gtggacagaa gcccagagac ttgactgctg gagaggtggt     120
caagtgtccc tcaaggtcag taatgatggg cctacactga ttggtgcaaa tgcctccttc     180
tctattgcct tgaacttccc tggaagccaa aaggtattgc cagatgggca ggttatctgg     240
gtcaacaata ccatcatcaa tgggagccag gtgtggggag acagccagt gtatccccag      300
gaaactgacg atgcctgcat cttccctgat ggtggacctt gcccatctgg ctcttggtct     360
cagaagagaa gctttgttta tgtctggaag acctgggggcc aatactggca agttctaggg    420
ggcccagtgt ctgggctgag cattgggaca ggcagggcaa tgctgggcac acacaccatg     480
gaagtgactg tctaccatcg ccggggatcc cggagctatg tgcctcttgc tcattccagc     540
tcagccttca ccattactga ccaggtgcct ttctccgtga gcgtgtccca gttgcgggcc     600
ttggatggag ggaacaagca cttcctgaga aat                                  633

<210> SEQ ID NO 16
<211> LENGTH: 211
<212> TYPE: PRT
<213> ORGANISM: Homo sapiens

<400> SEQUENCE: 16

Lys Val Pro Arg Asn Gln Asp Trp Leu Gly Val Ser Arg Gln Leu Arg
1               5                   10                  15

Thr Lys Ala Trp Asn Arg Gln Leu Tyr Pro Glu Trp Thr Glu Ala Gln
            20                  25                  30

Arg Leu Asp Cys Trp Arg Gly Gly Gln Val Ser Leu Lys Val Ser Asn
        35                  40                  45

Asp Gly Pro Thr Leu Ile Gly Ala Asn Ala Ser Phe Ser Ile Ala Leu
    50                  55                  60

Asn Phe Pro Gly Ser Gln Lys Val Leu Pro Asp Gly Gln Val Ile Trp

|   |   |   |   | 65 |   |   |   |   | 70 |   |   |   |   | 75 |   |   |   |   | 80 |
|---|---|---|---|---|---|---|---|---|---|---|---|---|---|---|---|---|---|---|---|

Val Asn Asn Thr Ile Ile Asn Gly Ser Gln Val Trp Gly Gly Gln Pro
                            85                  90                  95

Val Tyr Pro Gln Glu Thr Asp Asp Ala Cys Ile Phe Pro Asp Gly Gly
            100                 105                 110

Pro Cys Pro Ser Gly Ser Trp Ser Gln Lys Arg Ser Phe Val Tyr Val
            115                 120                 125

Trp Lys Thr Trp Gly Gln Tyr Trp Gln Val Leu Gly Gly Pro Val Ser
    130                 135                 140

Gly Leu Ser Ile Gly Thr Gly Arg Ala Met Leu Gly Thr His Thr Met
145                 150                 155                 160

Glu Val Thr Val Tyr His Arg Arg Gly Ser Arg Ser Tyr Val Pro Leu
                165                 170                 175

Ala His Ser Ser Ser Ala Phe Thr Ile Thr Asp Gln Val Pro Phe Ser
            180                 185                 190

Val Ser Val Ser Gln Leu Arg Ala Leu Asp Gly Gly Asn Lys His Phe
            195                 200                 205

Leu Arg Asn
    210

<210> SEQ ID NO 17
<211> LENGTH: 1416
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (104)..(104)
<223> OTHER INFORMATION: may be cytosine

<400> SEQUENCE: 17
ctgcagaaca ccatgaaccc aagtgctgcc gtcattttct gcctcatcct gctgggtctg      60
agtgggactc aagggatcct cgacatggca agcaactacg actgttgcct ctcgtacata     120
cagacgcctc ttccttccag agctattgtg ggtttcacaa gacagatggc cgatgaagct     180
tgtgacatta atgctatcat ctttcacacg aagaaaagaa atctgtgtg cgctgatcca      240 aagcagaact gggtgaaaag ggctgtgaac ctcctcagcc taagagtcaa gaagatggaa     300
ttcaacgacg ctcaggcgcc gaagagtctc gaggctagaa agtacccag aaaccaggac      360 tggcttggtg tctcaaggca actcagaacc aaagcctgga caggcagct gtatccagag      420 tggacagaag cccagagact tgactgctgg agaggtggtc aagtgtccct caaggtcagt     480
aatgatgggc tacactgat tggtgcaaat gcctccttct ctattgcctt gaacttccct      540
ggaagccaaa aggtattgcc agatgggcag gttatctggg tcaacaatac catcatcaat     600
gggagccagg tgtggggagg acagccagtg tatccccagg aaactgacga tgcctgcatc     660
ttccctgatg gtggaccttg cccatctggc tcttggtctc agaagagaag ctttgtttat     720
gtctggaaga cctggggcca atactggcaa gttctagggg gcccagtgtc tgggctgagc     780
attgggacag gcagggcaat gctgggcaca cacaccatgg aagtgactgt ctaccatcgc     840
cggggatccc ggagctatgt gcctcttgct cattccagct cagccttcac cattactgac     900
caggtgcctt tctccgtgag cgtgtcccag ttgcgggcct tggatggagg gaacaagcac     960
ttcctgagaa atctagaaat ggagttcaac gacgctcagg cgccgaagag tctcgaagct    1020
gggctgctcg gacccaacgg gacccagccc cagatcgcca actgcagcgt gatgactttt    1080

```
tttgtgtggc tccattatta ttctgttcga gacacattat taggtccagg acgcccctat    1140
aaggccattg atttctctca ccaagggcct gcctttgtca cgtggcacag gtaccatctg    1200
ttgtggctgg aaagagaact ccagagactc actggcaatg agtcctttgc gttgccctac    1260
tggaactttg caaccgggaa gaacgagtgt gacgtgtgca cagacgagct gcttggagca    1320
gcgcggccgc agtcgactct agagagatcc gcagaagaac agaaactgat ctcagaagag    1380
gatctggccc accaccatca ccatcactaa cccggg                              1416
```

<210> SEQ ID NO 18
<211> LENGTH: 465
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (31)..(31)
<223> OTHER INFORMATION: may be serine

<400> SEQUENCE: 18

```
Met Asn Pro Ser Ala Ala Val Ile Phe Cys Leu Ile Leu Leu Gly Leu
1               5                   10                  15

Ser Gly Thr Gln Gly Ile Leu Asp Met Ala Ser Asn Tyr Asp Cys Cys
            20                  25                  30

Leu Ser Tyr Ile Gln Thr Pro Leu Pro Ser Arg Ala Ile Val Gly Phe
        35                  40                  45

Thr Arg Gln Met Ala Asp Glu Ala Cys Asp Ile Asn Ala Ile Ile Phe
    50                  55                  60

His Thr Lys Lys Arg Lys Ser Val Cys Ala Asp Pro Lys Gln Asn Trp
65                  70                  75                  80

Val Lys Arg Ala Val Asn Leu Leu Ser Leu Arg Val Lys Lys Met Glu
                85                  90                  95

Phe Asn Asp Ala Gln Ala Pro Lys Ser Leu Glu Ala Arg Lys Val Pro
            100                 105                 110

Arg Asn Gln Asp Trp Leu Gly Val Ser Arg Gln Leu Arg Thr Lys Ala
        115                 120                 125

Trp Asn Arg Gln Leu Tyr Pro Glu Trp Thr Glu Ala Gln Arg Leu Asp
    130                 135                 140

Cys Trp Arg Gly Gly Gln Val Ser Leu Lys Val Ser Asn Asp Gly Pro
145                 150                 155                 160

Thr Leu Ile Gly Ala Asn Ala Ser Phe Ser Ile Ala Leu Asn Phe Pro
                165                 170                 175

Gly Ser Gln Lys Val Leu Pro Asp Gly Gln Val Ile Trp Val Asn Asn
            180                 185                 190

Thr Ile Ile Asn Gly Ser Gln Val Trp Gly Gly Gln Pro Val Tyr Pro
        195                 200                 205

Gln Glu Thr Asp Asp Ala Cys Ile Phe Pro Asp Gly Gly Pro Cys Pro
    210                 215                 220

Ser Gly Ser Trp Ser Gln Lys Arg Ser Phe Val Tyr Val Trp Lys Thr
225                 230                 235                 240

Trp Gly Gln Tyr Trp Gln Val Leu Gly Gly Pro Val Ser Gly Leu Ser
                245                 250                 255

Ile Gly Thr Gly Arg Ala Met Leu Gly Thr His Thr Met Glu Val Thr
            260                 265                 270

Val Tyr His Arg Arg Gly Ser Arg Ser Tyr Val Pro Leu Ala His Ser
        275                 280                 285
```

```
Ser Ser Ala Phe Thr Ile Thr Asp Gln Val Pro Phe Ser Val Ser Val
    290                 295                 300

Ser Gln Leu Arg Ala Leu Asp Gly Gly Asn Lys His Phe Leu Arg Asn
305                 310                 315                 320

Leu Glu Met Glu Phe Asn Asp Ala Gln Ala Pro Lys Ser Leu Glu Ala
                325                 330                 335

Gly Leu Leu Gly Pro Asn Gly Thr Gln Pro Gln Ile Ala Asn Cys Ser
            340                 345                 350

Val Tyr Asp Phe Phe Val Trp Leu His Tyr Tyr Ser Val Arg Asp Thr
        355                 360                 365

Leu Leu Gly Pro Gly Arg Pro Tyr Lys Ala Ile Asp Phe Ser His Gln
    370                 375                 380

Gly Pro Ala Phe Val Thr Trp His Arg Tyr His Leu Leu Trp Leu Glu
385                 390                 395                 400

Arg Glu Leu Gln Arg Leu Thr Gly Asn Glu Ser Phe Ala Leu Pro Tyr
                405                 410                 415

Trp Asn Phe Ala Thr Gly Lys Asn Glu Cys Asp Val Cys Thr Asp Glu
            420                 425                 430

Leu Leu Gly Ala Ala Arg Pro Gln Ser Thr Leu Glu Arg Ser Ala Glu
        435                 440                 445

Glu Gln Lys Leu Ile Ser Glu Glu Asp Leu Ala His His His His His
    450                 455                 460

His
465

<210> SEQ ID NO 19
<211> LENGTH: 1422
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (110)..(110)
<223> OTHER INFORMATION: may be cytosine

<400> SEQUENCE: 19
ctgcagaaca ccatggatgc aatgaagaga gggctctgct gtgtgctgct gctgtgtgga      60
gcagtcttcg tttcgcccag cctcgacatg gcagcaagca ctttgactgc tgtcttggga     120
tacacagacc gtattcttca tcctaaattt attgtgggct tcacacggca gctggccaat     180
gaaggctgtg acatcaatgc tatcatcttt cacacaaaga aaagttgtc tgtgtgcgca     240 aatccaaaac agacttgggt gaaatatatt gtgcgtctcc tcagtaaaaa agtcaagaac     300
atggaattca cgacgctca ggcgccgaag agtctcgagg ctagaaaagt acccagaaac     360
caggactggc ttggtgtctc aaggcaactc agaaccaaag cctggaacag cagctgtat     420 ccagagtgga cagaagccca gagacttgac tgctggagag tggtcaagt gtccctcaag     480 gtcagtaatg atgggcctac actgattggt gcaaatgcct ccttctctat gccttgaac     540 ttccctggaa gccaaaaggt attgccagat gggcaggtta tctgggtcaa caataccatc     600
atcaatggga gccaggtgtg gggaggacag ccagtgtatc cccaggaaac tgacgatgcc     660
tgcatcttcc ctgatggtgg accttgccca tctggctctt ggtctcagaa gagaagcttt     720
gtttatgtct ggaagacctg ggccaatac tggcaagttc tagggggccc agtgtctggg     780
ctgagcattg gacaggcag ggcaatgctg ggcacacaca ccatggaagt gactgtctac     840
```

-continued

| | |
|---|---|
| catcgccggg gatcccggag ctatgtgcct cttgctcatt ccagctcagc cttcaccatt | 900 |
| actgaccagg tgcctttctc cgtgagcgtg tcccagttgc gggccttgga tggagggaac | 960 |
| aagcacttcc tgagaaatct agaaatggag ttcaacgacg ctcaggcgcc gaagagtctc | 1020 |
| gaagctggcc tgcttgggcc aatggaacc cagccgcagt ttgccaactg cagtgtttat | 1080 |
| gattttttg tgtggctcca ttattattct gttagagata cattattagg accaggacgc | 1140 |
| ccctacaggg ccatagattt ctcacatcaa ggacctgcat tgttacctg caccggtac | 1200 |
| catttgttgt gtctggaaag agatctccag cgactcattg gcaatgagtc ttttgctttg | 1260 |
| ccctactgga actttgccac tgggaggaac gagtgtgatg tgtgtacaga ccagctgttt | 1320 |
| ggggcagcgc ggccgcagtc gactctagag agatccgcag aagaacagaa actgatctca | 1380 |
| gaagaggatc tggcccacca ccatcaccat cactaacccg gg | 1422 |

```
<210> SEQ ID NO 20
<211> LENGTH: 467
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (33)..(33)
<223> OTHER INFORMATION: may be serine

<400> SEQUENCE: 20
```

Met Asp Ala Met Lys Arg Gly Leu Cys Cys Val Leu Leu Cys Gly
1               5                   10                  15

Ala Val Phe Val Ser Pro Ser Leu Asp Met Ala Ala Ser Asn Phe Asp
                20                  25                  30

Cys Cys Leu Gly Tyr Thr Asp Arg Ile Leu His Pro Lys Phe Ile Val
            35                  40                  45

Gly Phe Thr Arg Gln Leu Ala Asn Glu Gly Cys Asp Ile Asn Ala Ile
        50                  55                  60

Ile Phe His Thr Lys Lys Lys Leu Ser Val Cys Ala Asn Pro Lys Gln
65                  70                  75                  80

Thr Trp Val Lys Tyr Ile Val Arg Leu Leu Ser Lys Lys Val Lys Asn
                85                  90                  95

Met Glu Phe Asn Asp Ala Gln Ala Pro Lys Ser Leu Glu Ala Arg Lys
            100                 105                 110

Val Pro Arg Asn Gln Asp Trp Leu Gly Val Ser Arg Gln Leu Arg Thr
        115                 120                 125

Lys Ala Trp Asn Arg Gln Leu Tyr Pro Glu Trp Thr Glu Ala Gln Arg
    130                 135                 140

Leu Asp Cys Trp Arg Gly Gly Gln Val Ser Leu Lys Val Ser Asn Asp
145                 150                 155                 160

Gly Pro Thr Leu Ile Gly Ala Asn Ala Ser Phe Ser Ile Ala Leu Asn
                165                 170                 175

Phe Pro Gly Ser Gln Lys Val Leu Pro Asp Gly Gln Val Ile Trp Val
            180                 185                 190

Asn Asn Thr Ile Ile Asn Gly Ser Gln Val Trp Gly Gly Gln Pro Val
        195                 200                 205

Tyr Pro Gln Glu Thr Asp Asp Ala Cys Ile Phe Pro Asp Gly Gly Pro
    210                 215                 220

Cys Pro Ser Gly Ser Trp Ser Gln Lys Arg Ser Phe Val Tyr Val Trp
225                 230                 235                 240

```
Lys Thr Trp Gly Gln Tyr Trp Gln Val Leu Gly Pro Val Ser Gly
                245                 250                 255

Leu Ser Ile Gly Thr Gly Arg Ala Met Leu Gly Thr His Thr Met Glu
        260                 265                 270

Val Thr Val Tyr His Arg Arg Gly Ser Arg Ser Tyr Val Pro Leu Ala
            275                 280                 285

His Ser Ser Ser Ala Phe Thr Ile Thr Asp Gln Val Pro Phe Ser Val
        290                 295                 300

Ser Val Ser Gln Leu Arg Ala Leu Asp Gly Asn Lys His Phe Leu
305                 310                 315                 320

Arg Asn Leu Glu Met Glu Phe Asn Asp Ala Gln Ala Pro Lys Ser Leu
                325                 330                 335

Glu Ala Gly Leu Leu Gly Pro Asn Gly Thr Gln Pro Gln Phe Ala Asn
            340                 345                 350

Cys Ser Val Tyr Asp Phe Phe Val Trp Leu His Tyr Tyr Ser Val Arg
        355                 360                 365

Asp Thr Leu Leu Gly Pro Gly Arg Pro Tyr Arg Ala Ile Asp Phe Ser
    370                 375                 380

His Gln Gly Pro Ala Phe Val Thr Trp His Arg Tyr His Leu Leu Cys
385                 390                 395                 400

Leu Glu Arg Asp Leu Gln Arg Leu Ile Gly Asn Glu Ser Phe Ala Leu
                405                 410                 415

Pro Tyr Trp Asn Phe Ala Thr Gly Arg Asn Glu Cys Asp Val Cys Thr
            420                 425                 430

Asp Gln Leu Phe Gly Ala Ala Arg Pro Gln Ser Thr Leu Glu Arg Ser
        435                 440                 445

Ala Glu Glu Gln Lys Leu Ile Ser Glu Glu Asp Leu Ala His His His
    450                 455                 460

His His His
465

<210> SEQ ID NO 21
<211> LENGTH: 17
<212> TYPE: PRT
<213> ORGANISM: Gaussia princeps

<400> SEQUENCE: 21

Met Gly Val Lys Val Leu Phe Ala Leu Ile Cys Ile Ala Val Ala Glu
1               5                   10                  15

Ala

<210> SEQ ID NO 22
<211> LENGTH: 18
<212> TYPE: PRT
<213> ORGANISM: Homo sapiens

<400> SEQUENCE: 22

Met Lys Trp Val Thr Phe Ile Ser Leu Leu Phe Leu Phe Ser Ser Ala
1               5                   10                  15

Tyr Ser

<210> SEQ ID NO 23
<211> LENGTH: 18
<212> TYPE: PRT
<213> ORGANISM: Homo sapiens

<400> SEQUENCE: 23
```

```
Met Ala Phe Leu Trp Leu Leu Ser Cys Trp Ala Leu Leu Gly Thr Thr
1               5                   10                  15

Phe Gly

<210> SEQ ID NO 24
<211> LENGTH: 14
<212> TYPE: PRT
<213> ORGANISM: Homo sapiens

<400> SEQUENCE: 24

Met Gln Leu Leu Ser Cys Ile Ala Leu Ile Leu Ala Leu Val
1               5                   10

<210> SEQ ID NO 25
<211> LENGTH: 15
<212> TYPE: PRT
<213> ORGANISM: Homo sapiens

<400> SEQUENCE: 25

Met Asn Leu Leu Leu Ile Leu Thr Phe Val Ala Ala Ala Val Ala
1               5                   10                  15

<210> SEQ ID NO 26
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 26

Met Asp Ala Met Lys Arg Gly Leu Cys Cys Val Leu Leu Leu Cys Gly
1               5                   10                  15

Ala Val Phe Val Ser Pro Ser
            20
```